United States Patent
Marti et al.

(10) Patent No.: US 7,563,864 B2
(45) Date of Patent: Jul. 21, 2009

(54) PROLYL ENDOPEPTIDASE MEDIATED DESTRUCTION OF T CELL EPITOPES IN WHOLE GLUTEN

(75) Inventors: Thomas Marti, Baden (CH); Øyvind Molberg, Oslo (NO); Ludvig M. Sollid, Bekkestua (NO)

(73) Assignees: Celiac Sprue Research Foundation, Mountain View, CA (US); Universitetet I Oslo, Oslo (NO)

( * ) Notice: Subject to any disclaimer, the term of this patent is extended or adjusted under 35 U.S.C. 154(b) by 613 days.

(21) Appl. No.: 11/115,935

(22) Filed: Apr. 26, 2005

(65) Prior Publication Data

US 2006/0286601 A1 Dec. 21, 2006

Related U.S. Application Data

(60) Provisional application No. 60/565,686, filed on Apr. 26, 2004.

(51) Int. Cl.
  C07K 7/00 (2006.01)
  C07K 14/00 (2006.01)
  C12N 9/00 (2006.01)
  C12N 9/10 (2006.01)

(52) U.S. Cl. .................. 530/324; 530/325; 530/326; 530/327; 530/328; 530/402; 530/403; 435/183; 435/193

(58) Field of Classification Search .................. None
See application file for complete search history.

(56) References Cited

U.S. PATENT DOCUMENTS

| | | | |
|---|---|---|---|
| 5,834,428 | A | 11/1998 | Drucker |
| 6,197,356 | B1 | 3/2001 | Girsh |
| 6,319,726 | B1 | 11/2001 | Schuppan et al. |
| 6,410,550 | B1 | 6/2002 | Coe et al. |
| 7,144,569 | B1 | 12/2006 | Anderson et al. |
| 2001/0036639 | A1 | 11/2001 | Fine |
| 2004/0241664 | A1 | 12/2004 | Dekker et al. |
| 2006/0178299 | A1 | 8/2006 | Anderson et al. |

FOREIGN PATENT DOCUMENTS

| | | |
|---|---|---|
| EP | 0 905 518 A1 | 3/1999 |
| WO | WO 94/26774 | 11/1994 |
| WO | 01/25793 | 4/2001 |
| WO | WO 01/25793 A2 | 4/2001 |
| WO | WO 03/068170 A2 | 8/2003 |

OTHER PUBLICATIONS

Casadio, R et al. Eur. J. Biochem. [1999] 262:672-679.*
Vader, Willeminj; et al, "The HLA-DQ2 gene dose effect in celiac disease is directly related to the magnitude and breadth of gluten-specific T cell responses", PNAS, Oct. 14, 2003, vol. 100, No. 21, pp. 12390-12395.
Arentz-Hansen, Helene; et al., "Celiac Lesion T Cells Recognize Epitopes That Cluster in Regions of Gliadins Rick in Proline Residues", Gastroenterology, 2002, vol. 123, No. 3, pp. 803-809.
Sjostrom, H; et al., "Identification of a Gliadin T-Cell Epitope in Coeliac Disease: General Importance of Gliadin Deamidation for Intestinal T-Cell Recognition", Scand. J. Immunol, 1998, 48, pp. 111-115.
Ahnen, et al., "Intestinal aminooligopeptidase in vivo synthesis on intracellular membranes of rat jejunum," (1982) The Journal of Biological Chemistry, 257:12129-12935.
Arentz-Hansen, et al., "The intestinal T cell response to α-gliadin in adult celiac disease is focused on a single deamidated glutamine targeted by tissue transolutaminase," (2000) The Journal of Experimental Medicine, 191:603-612.
Bordusa, et al., "The specificity of prolyl endopeptidase from Flavobacterium meningoseptum: mapping the s' subsites by positional scanning via acyl transfer," (1998) Bioorganic & Medicinal Chemistry, 6:1775-1780.
Lahteenoja, et al., "Local challenge on oral mucosa with an α-gliadin related synthetic peptide in patients with celiac disease," (2000) American Journal of Gastroenterology, 95:2880.
Schuppan and Detlef, "Special reports and reviews: Current concepts of celiac disease pathogenesis," (2000) Gastroenterology, 119:234-42.
Wieser, "The precipitating factor in coeliac disease," (1995) Ballière's Clinical Gastroenterology, 9(2):191-207.
Yoshimoto, et al., "Prolyl endopeptidase from Flavobacterium meningosepticum: cloning and sequencing of the enzyme gene," (1991) The Journal of Biochemistry, 110:873-878.
Database Derwent, "HLA-bindng oligopeptide and an immuno-regulator contgit—used in the treatment of auto-immune disease," (1996)ACC-No. 1996-329479.

* cited by examiner

Primary Examiner—Eileen B O'Hara
Assistant Examiner—F. Pierre VanderVegt
(74) Attorney, Agent, or Firm—Bozicevic, Field & Francis LLP; Pamela J. Sherwood

(57) ABSTRACT

Celiac Sprue and/or dermatitis herpetiformis are treated by interfering with HLA binding of immunogenic gluten peptides. The antigenicity of gluten oligopeptides and the ill effects caused by an immune response thereto are decreased by administration of an HLA-binding peptide inhibitor. Such inhibitors are analogs of immunogenic gluten peptides and (i) retain the ability to bind tightly to HLA molecules; (ii) retain the proteolytic stability of these peptides; but (iii) are unable to activate disease-specific T cells.

7 Claims, 6 Drawing Sheets

PROLYL ENDOPEPTIDASE MEDIATED DESTRUCTION OF T CELL EPITOPES IN WHOLE GLUTEN

BACKGROUND OF THE INVENTION

Figure 1:
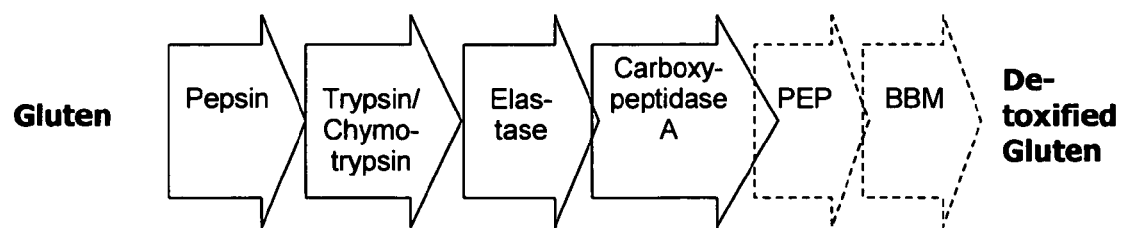

In 1953, it was first recognized that ingestion of gluten, a common dietary protein present in wheat, barley and rye causes a disease called Celiac Sprue in sensitive individuals. Gluten is a complex mixture of glutamine- and proline-rich gliadin and glutenin molecules and is thought to be responsible for induction of Celiac Sprue. Ingestion of such proteins by sensitive individuals produces flattening of the normally luxurious, rug-like, epithelial lining of the small intestine known to be responsible for efficient and extensive terminal digestion of peptides and other nutrients. Other clinical symptoms of Celiac Sprue include fatigue, chronic diarrhea, malabsorption of nutrients, weight loss, abdominal distension, anemia, as well as an enhanced risk for the development of osteoporosis and intestinal malignancies such as lymphoma and carcinoma. The disease has an incidence of approximately 1 in 200 in European populations and is believed to be significantly under diagnosed in other populations.

A related disease is dermatitis herpetiformis, which is a chronic eruption of the skin characterized by clusters of intensely pruritic vesicles, papules, and urticaria-like lesions. IgA deposits occur in almost all normal-appearing and perilesional skin. Asymptomatic gluten-sensitive enteropathy is found in 75 to 90% of patients and in some of their relatives. Onset is usually gradual. Itching and burning are severe, and scratching often obscures the primary lesions with eczematization of nearby skin, leading to an erroneous diagnosis of eczema. Strict adherence to a gluten-free diet for prolonged periods may control the disease in some patients, obviating or reducing the requirement for drug therapy. Dapsone, sulfapyridine, and colchicines are sometimes prescribed for relief of itching.

Celiac Sprue (CS) is generally considered to be an autoimmune disease and the antibodies found in the serum of the patients support the theory that the disease is immunological in nature. Antibodies to tissue transglutaminase (TG2, tTGase or tTG) and gliadin appear in almost 100% of the patients with active CS, and the presence of such antibodies, particularly of the IgA class, has been used in diagnosis of the disease.

The large majority of patients express the HLA-DQ2 [DQ (a1*05, b*02)] and/or DQ8 [DQ(a1*03, b1*0302)] molecules. It is believed that intestinal damage is caused by interactions between specific gliadin oligopeptides and the HLA-DQ2 or DQ8 antigen, which in turn induce proliferation of T lymphocytes in the sub-epithelial layers. T helper 1 cells and cytokines apparently play a major role in a local inflammatory process leading to villous atrophy of the small intestine.

At the present time, there is no good therapy for the disease, except to avoid completely all foods containing gluten. Although gluten withdrawal has transformed the prognosis for children and substantially improved it for adults, some people still die of the disease, mainly adults who had severe disease at the outset. A leading cause of death is lymphoreticular disease, especially intestinal lymphoma. It is not known whether a gluten-free diet diminishes this risk. Apparent clinical remission is often associated with histologic relapse that is detected only by review biopsies or by increased titers of antibodies to tTGase (also called EMA antibodies).

Gluten is so widely used, for example, in commercial soups, sauces, ice creams, hot dogs, and other foodstuffs, that patients need detailed lists of foodstuffs to avoid and expert advice from a dietitian familiar with celiac disease. Ingesting even small amounts of gluten may prevent remission or induce relapse. Supplementary vitamins, minerals, and hematinics may also be required, depending on deficiency. A few patients respond poorly or not at all to gluten withdrawal, either because the diagnosis is incorrect or because the disease is refractory. In the latter case, oral corticosteroids (e.g., prednisone 10 to 20 mg bid) may induce response.

In view of the serious and widespread nature of Celiac Sprue and the difficulty of removing gluten from the diet, better methods of treatment are of great interest. In particular, there is a need for treatment methods that allow the Celiac Sprue individual to eat gluten-containing foodstuffs without ill effect or at least to tolerate such foodstuffs in small or moderate quantities without inducing relapse. The present invention meets this need for better therapies for Celiac Sprue.

SUMMARY OF THE INVENTION

In one aspect, the present invention provides methods for treating Celiac Sprue and/or dermatitis herpetiformis and the symptoms thereof by administration of an HLA-binding peptide inhibitor to the patient.

In another aspect, the invention provides methods for screening candidate compounds to determine their suitability for use in the subject methods, by assessing the ability of a candidate agent for its ability to bind to HLA molecules, and/or to inhibit the activity of T cells reactive against gluten antigens.

In another aspect, the invention provides methods of determining the effectiveness of a potential treatment, by treating one or more of the peptides provided herein, and determining the responsiveness of T cell clones to the material. The material is generally treated with tissue transglutaminase TG2 prior to T cell stimulation.

In another aspect, the invention provides methods of identifying a second protease capable of enhancing the therapeutic efficacy of the *Flavobacterium meningosepticum* PEP.

The peptides provided herein also find use in diagnostic assays, as described in co-pending application U.S. Ser. No. 03/37434, herein specifically incorporated by reference.

These and other aspects and embodiments of the invention and methods for making and using the invention are described in more detail in the description of the drawings and the invention, the examples, the claims, and the drawings that follow.

BRIEF DESCRIPTION OF THE DRAWINGS

FIG. 1. Overall strategy for simulating enzymatic detoxification of gluten. PEP, Prolyl Endopeptidase; BBM; Rat brush border membrane enzymes.

FIG. 2. $UV_{215}$ traces of PEP and BBM treated PTCEC gluten. Samples 1 to 7 are as described in Table 3. Sample 1, blue; 2, red; 3, black; 4, purple; 5, green; 6, light blue; 7, orange.

FIG. 3. 5-50 residue peptide sequences identified in samples 1-7 (Table 3) by LC-MS/MS with cross-correlation>1.5. Red bars represent the abundance of epitope containing peptides; blue bars represent the abundance of peptides containing no epitopes. The relative frequency of epitope-containing peptides is indicated by the black curve as a percentage of the total number of peptides in each sample.

Figure 4:
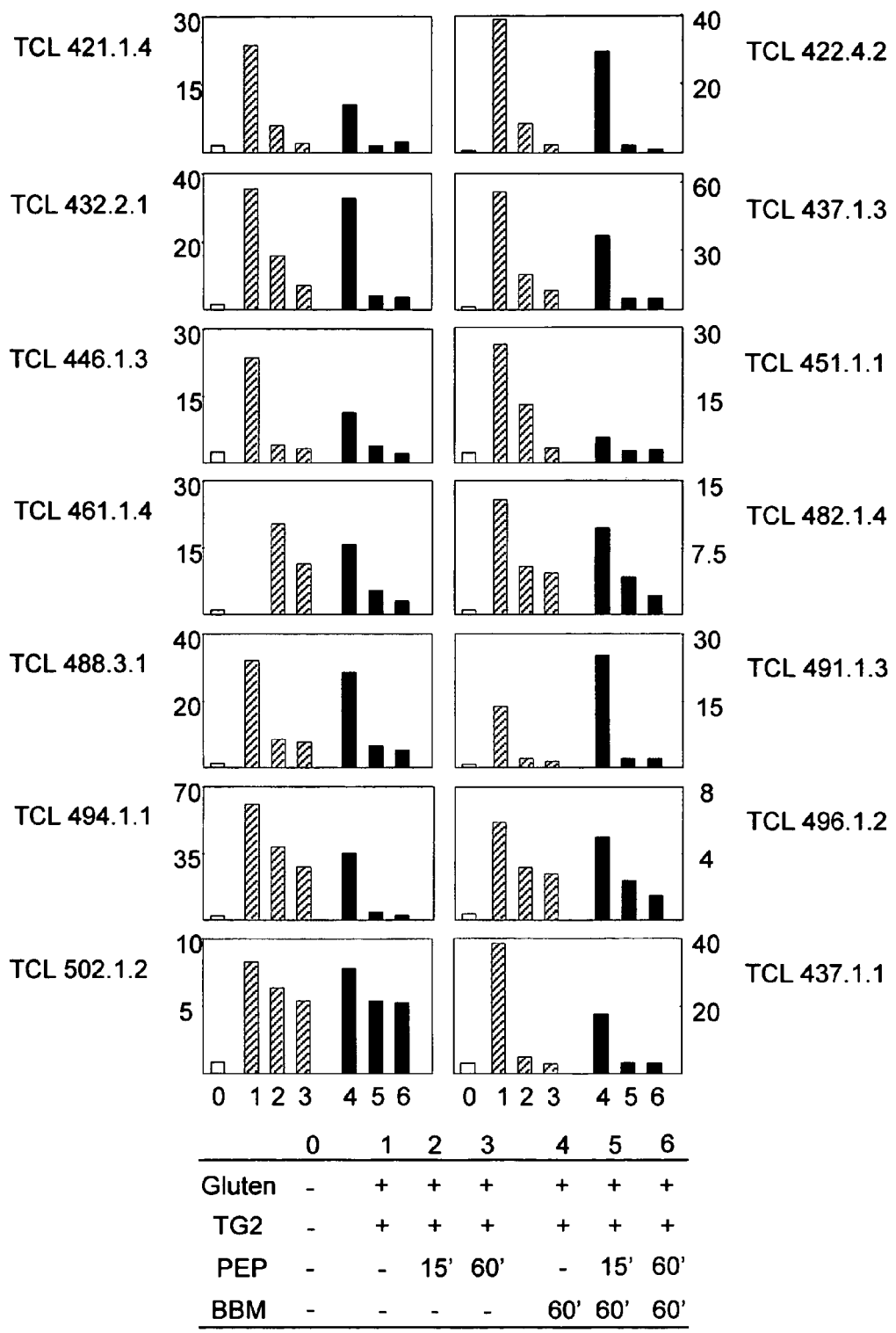

FIG. 4. Response of fourteen T cell lines challenged with 250 μg/ml gluten. The conditions under which individual gluten samples were treated are summarized in the table below.

Figure 5:
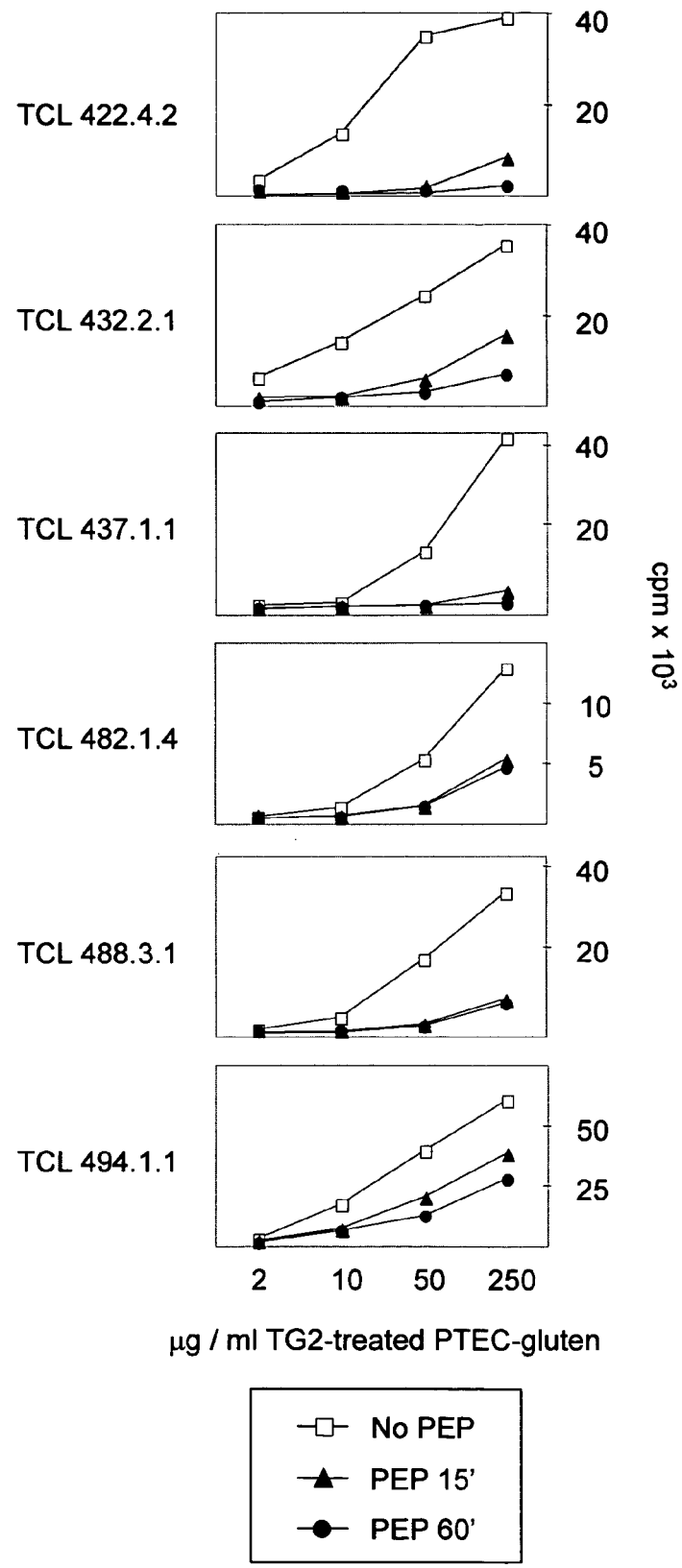

FIG. 5. Response of six polyclonal T cell lines to varying concentrations of TG2-treated PTCEC-gluten.

Figure 6:
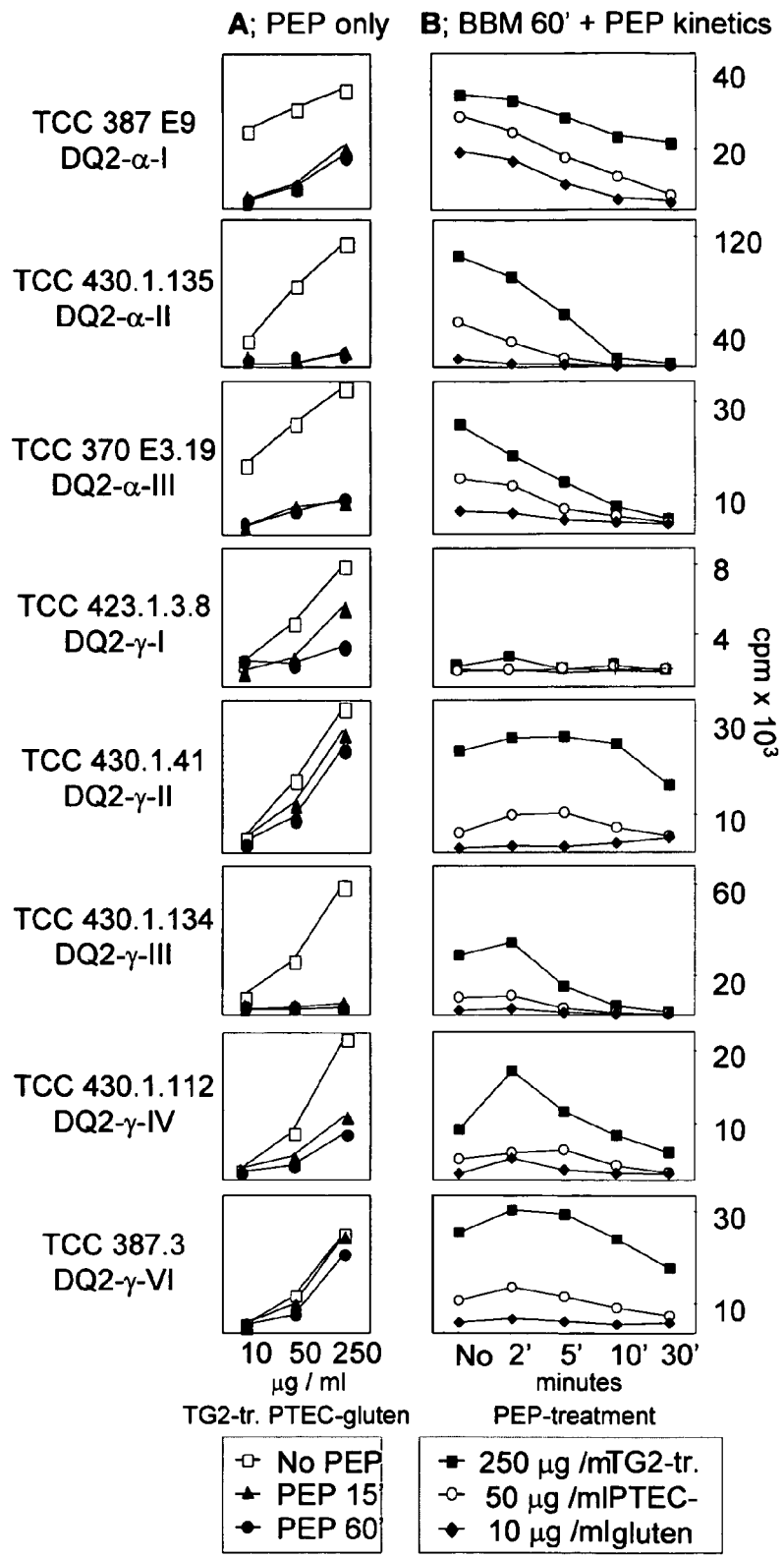

FIG. 6. Response of T cell clones to gluten. A: Titration with increasing concentrations of gluten. B: Kinetics of gluten destruction upon treatment with PEP (all samples treated with BBM for 60 min).

DETAILED DESCRIPTION OF THE EMBODIMENTS

Celiac Sprue and/or dermatitis herpetiformis are treated by interfering with HLA binding of immunogenic gluten peptides. Therapeutic benefit can be enhanced in some individuals by increasing the digestion of gluten oligopeptides, whether by pretreatment of foodstuffs to be ingested or by administration of an enzyme capable of digesting the gluten oligopeptides, together with administration of an HLA-binding peptide inhibitor. Gluten oligopeptides are highly resistant to cleavage by gastric and pancreatic peptidases such as pepsin, trypsin, chymotrypsin, and the like, and their prolonged presence in the digestive tract can induce an autoimmune response.

Peptides of interest in the methods of the invention include one, two, three, four, and up to all of the peptides set forth in Tables 1A, 1B and 1C.

Methods and compositions are provided for the administration of one or more HLA-binding peptide inhibitors to a patient suffering from Celiac Sprue and/or dermatitis herpetiformis. In some embodiments and for some individuals, the methods of the invention remove the requirement that abstention from ingestion of glutens be maintained to keep the disease in remission.

The subject methods are useful for both prophylactic and therapeutic purposes. Thus, as used herein, the term "treating" is used to refer to both prevention of disease, and treatment of a pre-existing condition. The treatment of ongoing disease, to stabilize or improve the clinical symptoms of the patient, is a particularly important benefit provided by the present invention. Such treatment is desirably performed prior to loss of function in the affected tissues; consequently, the prophylactic therapeutic benefits provided by the invention are also important. Evidence of therapeutic effect may be any diminution in the severity of disease, particularly diminution of the severity of such symptoms as fatigue, chronic diarrhea, malabsorption of nutrients, weight loss, abdominal distension, and anemia. Other disease indicia include the presence of antibodies specific for glutens, antibodies specific for tissue transglutaminase, the presence of pro-inflammatory T cells and cytokines, and degradation of the villus structure of the small intestine. Application of the methods and compositions of the invention can result in the improvement of any and all of these disease indicia of Celiac Sprue.

Patients that can benefit from the present invention include both adults and children. Children in particular benefit from prophylactic treatment, as prevention of early exposure to toxic gluten peptides can prevent development of the disease into its more severe forms. Children suitable for prophylaxis in accordance with the methods of the invention can be identified by genetic testing for predisposition, e.g. by HLA typing; by family history, and by other methods known in the art. As is known in the art for other medications, and in accordance with the teachings herein, dosages of the HLA-binding peptide inhibitors of the invention can be adjusted for pediatric use.

Because most proteases and peptidases are unable to hydrolyze the amide bonds of proline residues, the abundance of proline residues in gliadins and related proteins from wheat, rye and barley can constitute a major digestive obstacle for the enzymes involved. This leads to an increased concentration of relatively stable gluten derived oligopeptides in the gut. These stable gluten derived oligopeptides, called "immunogenic oligopeptides" herein, bind to MHC molecules, including HLA HLA-DQ2 or DQ8 molecules, to stimulate an immune response that results in the autoimmune disease aspects of Celiac Sprue. In some cases the enzyme tissue transglutaminase selectively deamidates certain glutamine residues in these peptides, thereby enhancing their potency for the DQ2 ligand binding pocket.

Among gluten proteins with potential harmful effect to Celiac Sprue patients are included the storage proteins of wheat, species of which include *Triticum aestivum; Triticum aethiopicum; Triticum baeoticum; Triticum militinae; Triticum monococcum; Triticum sinskajae; Triticum timopheevii; Triticum turgidum; Triticum urartu, Triticum vavilovii; Triticum zhukovskyi*; etc. A review of the genes encoding wheat storage proteins may be found in Colot (1990) *Genet Eng* (N Y) 12:225-41. Gliadin is the alcohol-soluble protein fraction of wheat gluten. Gliadins are typically rich in glutamine and proline, particularly in the N-terminal part. For example, the first 100 amino acids of α- and γ-gliadins contain ~35% and ~20% of glutamine and proline residues, respectively. Many wheat gliadins have been characterized, and as there are many strains of wheat and other cereals, it is anticipated that many more sequences will be identified using routine methods of molecular biology. Examples of gliadin sequences include but are not limited to wheat alpha gliadin sequences, for example as provided in Genbank, accession numbers AJ133612; AJ133611; AJ133610; AJ133609; AJ133608; AJ133607; AJ133606; AJ133605; AJ133604; AJ133603; AJ133602; D84341.1; U51307; U51306; U51304; U51303; U50984; and U08287. A sequence of wheat omega gliadin is set forth in Genbank accession number AF280605.

Among the immunogenic gluten oligopeptides that may be modified to generate an HLA-binding peptide inhibitor are included the peptide sequences set forth in Tables 1A, 1B and 1C; (SEQ ID NO:87) QLQPFPQPELPYP; the sequence (SEQ ID NO:88) PQPELPY; the sequence (SEQ ID NO:89) PFPQPELPYP, (SEQ ID NO:90) PQPELPYPQPQLP, (SEQ ID NO:91) PQQSFPEQQPP, (SEQ ID NO:92) VQGQGI-IQPEQPAQ, (SEQ ID NO:93) FPEQPQQPYPQQP, (SEQ ID NO:94) FPQQPEQPYPQQP, (SEQ ID NO:95) FSQPEQEF-PQPQ and longer peptides containing such sequences or multiple copies of such sequences. Gliadins, secalins and hordeins contain several (SEQ ID NO:96) PQPQLPY sequences or sequences similar thereto rich in Pro-Gln residues that are high-affinity substrates for tTGase. The tTGase catalyzed deamidation of such sequences increases their affinity for HLA-DQ2, the class II MHC allele present in >90% Celiac Sprue patients. Presentation of these deamidated sequences by DQ2 positive antigen presenting cells effectively stimulates proliferation of gliadin-specific T cells from intestinal biopsies of most Celiac Sprue patients, providing evidence for the proposed mechanism of disease progression in Celiac Sprue.

In one embodiment of the invention, methods are provided for determining the therapeutic treatment of an immunogenic peptide. Such methods may comprise detecting the ability of a candidate enzyme to digest gliadin peptides as set forth herein, and determining the ability of the enzyme to digest the peptides to non-toxic fragments, as assessed by responsiveness of T cells and T cell lines derived from Celiac Sprue patients. HPLC is optionally utilized to determine the length of digestions products.

Candidate T cells are described herein, or may be generated by methods known to those of skill in the art. Such lines may be restricted to a specific epitope, or may be polyclonal and respond to a variety of epitopes. Where patient specific analysis is performed, preferably the HLA restriction of the T cell is the same or similar to that of the patient.

Polypeptides of interest for such assays include gliadin proteins, fragments of gliadin proteins, and other gluten proteins, preferably peptides resistant to normal digestion. Specific peptides of interest include, without limitation, the peptide sequences set forth in Tables 1A, 1B and 1C.

A candidate treatment, e.g. digestion with a prolyl endopeptidase, is combined with one or more digestion-resistant peptides. The enzyme may be incubated from about 1 to about 4 hours. The polypeptides are treated, either before or after the candidate therapy, with tissue transglutaminase TG2. The reponsiveness of the T cells to the material is then determined, where the material is considered detoxified when the T cell response is reduced by at least about 50%, usually at least about 80%, more usually at least about 90% and preferably at least about 99%.

Diagnostic Aspects

Celiac Sprue and/or dermatitis herpetiformis are diagnosed by detecting digestion-refractory multivalent gluten oligopeptides, and/or T-cell proliferation produced by such oligopeptides in Celiac Sprue individuals. Gluten oligopeptides of interest are set forth in Tables 1A, 1, and 1C. Some of these peptides are multivalent, in that they comprise multiple T cell and/or antibody recognition epitopes. The natural covalent linkage of these epitopes in a polypeptide is a determinant of hyperantigenicity in susceptible individuals, and related to disease development and pathology. By providing for detection of such gluten oligopeptides; of antibodies specifically reactive thereto; and/or of T-cell proliferation produced by such oligopeptides in individuals, improved methods of diagnosing Celiac Sprue and/or dermatitis herpetiformis are provided.

These results provide the basis for a number of improved diagnostic methods for Celiac Sprue as well as a variety of reagents useful in those and other methods. The multivalent gluten oligopeptides described herein, including those set forth on Tables 1A, 1B and 1C; deamidated counterparts, derivatives, analogs, and conservatively modified variants thereof, are useful in stimulating T cells from Celiac Sprue patients for diagnostic purposes, and so are provided by the present invention in isolated and highly purified forms.

In one embodiment of the invention, a fusion protein comprising all or a portion of a mammalian tGase, including but not limited to human, bovine, equine, and porcine tTGase, is linked, usually covalently, to a multivalent gluten oligopeptide of the invention, wherein the linkage site is at a site for eventual deamidation. This fusion protein of the invention is a highly potent stimulator of T cells from Celiac Sprue patients in that the fusion protein exactly mimics the complexes formed in Celiac Sprue patients and is recognized by the anti-tTGase antibodies and by T cells in those patients. Such fusion proteins find use in the diagnostic methods of the invention.

Transglutaminases (EC 2.3.2.13) are a family of enzymes that catalyze the crosslinking of proteins by epsilon-gamma glutamyl lysine isopeptide bonds. The human haploid genome contains at least 8 distinct transglutaminases that are differentially expressed in time-space and tissue-specific ways, and these enzymes find use in the present invention. Although the overall primary structures of these enzymes appear to be quite different, they all share a common amino acid sequence at the active site (Y-G-Q-C- W) and a strict calcium dependence for their activity. The differences in the primary structures of these different transglutaminases are responsible for the diverse biologic functions that they play in physiologic processes.

Transglutaminases of particular interest include the human TG1, TG2 and TG3 enzymes. Keratinocyte transglutaminase, TG1, has the Genbank accession number D90287 (see Phillips et al. (1990) Proc. Natl. Acad. Sci. U.S.A. 87(23):9333-9337; Yamanishi et al. (1991) Biochem. Biophys. Res. Commun. 175(3):906-913). It is normally expressed in skin, and is involved in the barrier formation of keratinocytes. The human protein has a molecular mass of about 90 kD, having a 105-residue extension beyond the N terminus of the tissue transglutaminase (TG2). The deduced 813-amino acid sequence of the TG1 protein shares 49 to 53% homology with other transglutaminase proteins of known sequence.

Tissue transglutaminase 2 (TG2) has the Genbank accession number M55153, and encodes a 687 amino acid protein. It is expressed as a 3.6 kb mRNA in human endothelial cells. Tissue transglutaminase 3 (TG3) has the Genbank accession number L10386, and encodes a 692 amino acid protein. It is expressed as a 2.9-kb mRNA. The sequences of TG2 and TG3 find use in the recombinant production of the encoded polypeptide.

Transglutaminase polypeptides can be produced through isolation from natural sources, recombinant methods and chemical synthesis. In addition, functionally equivalent polypeptides may find use, where the equivalent polypeptide may contain deletions, additions or substitutions of amino acid residues that result in a silent change, thus producing a functionally equivalent differentially expressed on pathway gene product. Amino acid substitutions may be made on the basis of similarity in polarity, charge, solubility, hydrophobicity, hydrophilicity, and/or the amphipathic nature of the residues involved. "Functionally equivalent", as used herein, refers to a protein capable of exhibiting a substantially similar activity as the native polypeptide.

The polypeptides may be produced by recombinant DNA technology using techniques well known in the art. Methods that are well known to those skilled in the art can be used to construct expression vectors containing coding sequences and appropriate transcriptional/translational control signals. These methods include, for example, in vitro recombinant DNA techniques, synthetic techniques and in vivo recombination/genetic recombination. Alternatively, RNA capable of encoding the polypeptides of interest may be chemically synthesized.

As described in the examples, during normal digestion, a peptidase resistant oligopeptide core remains after exposure of glutens, e.g. gliadin, to normal digestive enzymes. Oligopeptide fragments of interest include fragments of at least about 20 contiguous amino acids, more usually at least about 33 contiguous amino acids, and may comprise 50 or more amino acids, and may extend further to comprise additional sequences. Examples of other peptidase resistant oligopeptides are provided in SEQ ID NO:5, 6, 7 and 10. Other examples of immunogenic gliadin oligopeptides are discussed by Wieser (1995) Baillieres Clin Gastroenterol 9(2): 191-207.

The multivalent gluten oligopeptides may be substituted with a glutamine analog at one or more positions, e.g. to enhance formation of a complex or covalent binding between tTGase and the peptide analog. Analogs useful in the preparation of substituted peptide for this purpose include the following:

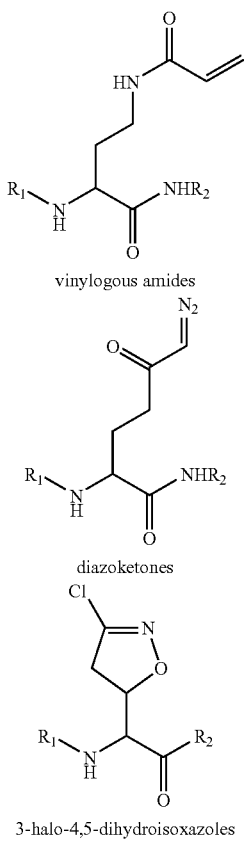

where R1 and R2 are independently selected from H, alkyl, alkenyl, cycloalkyl, aryl, heteroalkyl, heteroaryl, alkoxy, alkylthio, arakyl, aralkenyl, halo, haloalkyl, haloalkoxy, heterocyclyl, and heterocyclylalkyl groups. R1 and R2 may also comprise peptidic protecting groups. The amino acid analogs, 6-diazo-5-oxo-norleucine (Don), Azaserine (Aza), 6-thio(tetramethyl imidazoyl)-5-oxo-norleucine (Ton), 2-[2-thio(tetramethyl imidazoyl)-acyl]-2,3-diaminopropionic acid (Tad), acivicin (Aci)) and 3-chloro-4,5-dihydro-5-amino-isoxazole are also proposed as glutamine mimetics.

Polypeptide and Oligopeptide Compositions

The oligopeptides and proteins useful in the methods of the present invention may be prepared in accordance with conventional techniques, such as synthesis, recombinant techniques, isolation from natural sources, or the like. For example, solid-phase peptide synthesis involves the successive addition of amino acids to create a linear peptide chain (see Merrifield (1963) *J. Am. Chem. Soc.* 85:2149-2154). Production of a peptide or protein by recombinant DNA technology can also be performed. Thus, the oligopeptides may be prepared by in vitro synthesis, using conventional methods as known in the art. Various commercial synthetic apparatuses are available, for example, automated synthesizers by Applied Biosystems, Inc., Foster City, Calif., Beckman, and other manufacturers. By using synthesizers, naturally occurring amino acids may be substituted with unnatural amino acids. The particular sequence and the manner of preparation will be determined by convenience, economics, purity required, and the like.

The sequence of the provided epitopes, and of amino acids flanking epitopes, may be altered in various ways known in the art to generate targeted changes in sequence. Such "conservatively modified variants" will typically be functionally-preserved variants, which differ, usually in sequence, from the corresponding native or parent oligopeptide but still retain the biological activity, i.e., epitopic specificity. Variants may also include fragments of the oligopeptide that retain activity. Various methods known in the art may be used to generate targeted changes, e.g. phage display in combination with random and targeted mutations, introduction of scanning mutations, and the like.

A variant may be substantially similar to a native sequence, i.e. differing by at least one amino acid, and may differ by at least two but not more than about ten amino acids. The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); or (phenylalanine, tyrosine).

Modifications of interest that do not alter primary sequence include chemical derivatization of proteins, e.g., acetylation, or carboxylation. Also included in the subject invention are oligopeptides that have been modified using molecular biological techniques and synthetic chemistry so as to improve their resistance to proteolytic degradation, to acidic conditions such as those found in the stomach, or to optimize solubility properties or to render them more suitable as a therapeutic agent. For examples, the backbone of the peptidase may be cyclized to enhance stability (see Friedler et al., (2000) *J. Biol. Chem.* 275:23783-23789). Analogs of such proteins include those containing residues other than naturally occurring L-amino acids, e.g. D-amino acids or non-naturally occurring synthetic amino acids. If desired, various groups may be introduced into the oligopeptide during synthesis or during expression, which allow for linking to other molecules or to a surface. Thus cysteines can be used to make thioethers, histidines for linking to a metal ion complex, carboxyl groups for forming amides or esters, amino groups for forming amides, and the like.

Thus, the present invention includes oligopeptide analogs of the oligopeptides described by amino acid sequence herein. Such analogs contain at least one difference in amino acid sequence between the analog and native antigenic peptide. An L-amino acid from the native peptide may be altered to any other one of the 20 L-amino acids commonly found in proteins, any one of the corresponding D-amino acids, rare amino acids, such as 4-hydroxyproline, and hydroxylysine, or a non-protein amino acid, such as β-alanine and homoserine. Also included with the scope of the present invention are amino acids that have been altered by chemical means such as methylation (e.g., α-methylvaline), deamidation, amidation of the C-terminal amino acid by an alkylamine such as ethylamine, ethanolamine, and ethylene diamine, and acylation or methylation of an amino acid side chain function (e.g., acylation of the epsilon amino group of lysine), deimination of arginine to citrulline, isoaspartylation, or phosphorylation on serine, threonine, tyrosine or histidine residues. Candidate oligopeptide analogs may be screened for utility in a diagnostic method of the invention by an assay measuring competitive binding to MHC, and an assay measuring T cell proliferation. Those analogs that inhibit binding of the native peptides and that stimulate proliferation of autoreactive T cells are useful diagnostic reagents.

Oligopeptides and oligopeptide analogs may be synthesized by standard chemistry techniques, including synthesis by automated procedure. In general, peptide and peptide analogs are prepared by solid-phase peptide synthesis methodology which involves coupling each protected amino acid residue to a resin support, preferably a 4-methylbenzhydrylamine resin, by activation with dicyclohexylcarbodiimide to yield a peptide with a C-terminal amide. Alternatively, a chloromethyl resin (Merrifield resin) may be used to yield a peptide with a free carboxylic acid at the C-terminus. After the last residue has been attached, the protected peptide-resin is treated with hydrogen fluoride to cleave the peptide from the resin, as well as deprotect the side chain functional groups. Crude product can be further purified by gel filtration, HPLC, partition chromatography, or ion-exchange chromatography.

The oligopeptides may also be isolated and purified in accordance with conventional methods of recombinant synthesis, or from natural sources. A lysate may be prepared of the expression host and the lysate purified using HPLC, exclusion chromatography, gel electrophoresis, affinity chromatography, or other purification technique. For the most part, the compositions which are used will comprise at least 20% by weight of the desired product, more usually at least about 75% by weight, preferably at least about 95% by weight, and for diagnostic purposes, usually at least about 99.5% by weight, in relation to contaminants related to the method of preparation of the product and its purification. Usually, the percentages will be based upon total protein.

The present invention provides a variety of methods for diagnosing Celiac Sprue. In one embodiment, the diagnosis involves detecting the presence of a gluten oligopeptides digestion product, e.g. SEQ ID NO:12; deamidated counterparts there; a tTGase-linked counterpart thereof; etc., in a tissue, bodily fluid, or stool of an individual. The detecting step can be accomplished by use of a reagent, e.g. a T cell, that recognizes the indicated antigen, or by a cell that proliferates in the presence of the indicated antigen and suitable antigen presenting cells, wherein said antigen presenting cells are compatible with the MHC type of the proliferating cell, e.g. allogeneic cells, autologous cells, etc.

Samples may be obtained from patient tissue, which may be a mucosal tissue, including but not limited to oral, nasal, lung, and intestinal mucosal tissue, a bodily fluid, e.g. blood, sputum, urine, phlegm, lymph, and tears. One advantage of the present invention is that the antigens provided are such potent antigens, both for antibody-binding and T-cell stimulation, that the diagnostic methods of the invention can be employed with samples (tissue, bodily fluid, or stool) in which a Celiac Sprue diagnostic antibody, peptide, or T cell is present in very low abundance. This allows the methods of the invention to be practiced in ways that are much less invasive, much less expensive, and much less harmful to the Celiac Sprue individual.

Patients may be monitored for the presence of reactive T cells, using one or more multivalent oligopeptides as described above. The presence of such reactive T cells indicates the presence of an on-going immune response. The antigen used in the assays is a multivalent gluten oligopeptide as described above; including, without limitation, SEQ ID NO:12; deamidated counterparts; tTGase fusions thereof; and derivatives. Cocktails comprising multiple oligopeptides; panels of peptides; etc. may be also used. Overlapping peptides may be generated, where each peptide is frame-shifted from 1 to 5 amino acids, thereby generating a set of epitopes.

The diagnosis may determine the level of reactivity, e.g. based on the number of reactive T cells found in a sample, as compared to a negative control from a naive host, or standardized to a data curve obtained from one or more positive controls. In addition to detecting the qualitative and quantitative presence of antigen reactive T cells, the T cells may be typed as to the expression of cytokines known to increase or suppress inflammatory responses. While not necessary for diagnostic purposes, it may also be desirable to type the epitopic specificity of the reactive T cells, particularly for use in therapeutic administration of peptides.

T cells may be isolated from patient peripheral blood, lymph nodes, including peyer's patches and other gut-related lymph nodes, or from tissue samples as described above. Reactivity assays may be performed on primary T cells, or the cells may be fused to generate hybridomas. Such reactive T cells may also be used for further analysis of disease progression, by monitoring their in situ location, T cell receptor utilization, MHC cross-reactivity, etc. Assays for monitoring T cell responsiveness are known in the art, and include proliferation assays and cytokine release assays. Also of interest is an ELISA spot assay.

Proliferation assays measure the level of T cell proliferation in response to a specific antigen, and are widely used in the art. In one such assay, recipient lymph node, blood or spleen cells are obtained at one or more time points after transplantation. A suspension of from about $10^4$ to $10^7$ cells, usually from about $10^5$ to $10^6$ cells is prepared and washed, then cultured in the presence of a control antigen, and test antigens, as described above. The cells are usually cultured for several days. Antigen-induced proliferation is assessed by the monitoring the synthesis of DNA by the cultures, e.g. incorporation of $^3$H-thymidine during the last 18 H of culture.

T cell cytotoxic assays measure the numbers of cytotoxic T cells having specificity for the test antigen. Lymphocytes are obtained at different time points after transplantation. Alloreactive cytotoxic T cells are tested for their ability to kill target cells bearing recipient MHC class I molecules associated with peptides derived from a test antigen. In an exemplary assay, target cells presenting peptides from the test antigen, or a control antigen, are labeled with $Na^{51}CrO_4$. The target cells are then added to a suspension of candidate reactive lymphocytes. The cytotoxicity is measured by quantitating the release of $Na^{51}CrO_4$ from lysed cells. Controls for spontaneous and total release are typically included in the assay. Percent specific $^{51}Cr$ release may be calculated as follows: 100× (release by CTL−spontaneous release)/(total release−spontaneous release).

Enzyme linked immunosorbent assay (ELISA) and ELISA spot assays are used to determine the cytokine profile of reactive T cells, and may be used to monitor for the expression of such cytokines as IL-2, IL-4, IL-5, γIFN, etc. The capture antibodies may be any antibody specific for a cytokine of interest, where supernatants from the T cell proliferation assays, as described above, are conveniently used as a source of antigen. After blocking and washing, labeled detector antibodies are added, and the concentrations of protein present determined as a function of the label that is bound.

In one embodiment of the invention, the presence of reactive T cells is determined by injecting a dose of the 33-mer peptide, or a derivative or fragment thereof as described above, subcutaneously or sub-mucosally into a patient, for example into the oral mucosa (see Lahteenoja et al. (2000) *Am. J. Gastroenterology* 95:2880, herein incorporated by reference). A control comprising medium alone, or an unrelated protein is usually injected nearby at the same time. The site of injection is examined after a period of time, by biopsy or for the presence of a wheal.

A wheal at the site of injection is compared to that at the site of the control injection, usually by measuring the size of the wheal. The skin test readings may be assessed by a variety of objective grading systems. A positive result for the presence of an immune response will show an increased diameter at the site of polypeptide injection as compared to the control.

Where a biopsy is performed, the specimen is examined for the presence of increased numbers of immunologically active cells, e.g. T cells, B cells, mast cells, and the like. For example, methods of histochemistry and/or immunohistochemistry may be used, as is known in the art. The densities of cells, including antigen specific T cells, mast cells, B cells, etc. may be examined. It has been reported that increased numbers of intraepithelial $CD8^+$ T cells may correlate with gliadin reactivity.

Thus, in one aspect, the present invention provides a method for diagnosing Celiac Sprue in an individual who has not consumed gluten for an extended period of time, such time including but not limited to one day, one week, one month, and one year prior to the performance of the diagnostic method. The advantage conferred by this aspect of the invention is that current diagnosis of a Celiac Sprue individual typically involves a preliminary diagnosis, after which the individual is placed on a gluten-free diet. If the individual's symptoms abate after initiation of the gluten-free diet, then the individual is challenged with gluten, and another diagnostic test, such as an endoscopy or T cell proliferation assay, is performed to confirm the preliminary diagnosis. This re-challenge with gluten causes extreme discomfort to the Celiac Sprue individual. One important benefit provided by certain embodiments of the invention is that such a re-challenge need not be performed to diagnose Celiac Sprue, because even very low levels of 33-mer specific antibodies and T cell responders can be identified using the methods of the invention.

The subject methods are useful not only for diagnosing Celiac Sprue individuals but also for determining the efficacy of prophylactic or therapeutic methods for Celiac Sprue as well as the efficacy of food preparation or treatment methods aimed at removing glutens or similar substances from food sources. Thus, a Celiac Sprue individual efficaciously treated with a prophylactic or therapeutic drug or other therapy for Celiac Sprue tests more like a non-Celiac Sprue individual with the methods of the invention.

Experimental

Celiac Sprue has a clear HLA association. About 90-95% of the patients carry genes encoding the allelic HLA variant DQ2 (DQA1*05, DQB1*02), while most of the remaining patients express DQ8 (DQA1*03, DQB1*0302). Within the past few years several studies have mapped epitopes in gluten that stimulate intestinal CD4+ T cells from Celiac Sprue patients but not control subjects. These intestinal T cells are invariably restricted by HLA-DQ2- or DQ8, and focus on Gln and Pro rich peptides deamidated by tissue transglutaminase (TG2), the same enzyme that is the target of disease specific autoantibodies in Celiac Sprue. T cell epitopes have been identified in both the major classes of gluten proteins, the monomeric gliadins and the polymeric glutenins, but it is clear that a hierarchy exists between different epitopes. In particular, the α-gliadin epitopes are recognized by T cells from almost all patients, whereas responses to the γ-gliadin and glutenin epitopes are much less frequent in intestinal T cell lines derived from patients.

T cell epitopes are unevenly distributed in the sequences of gliadin proteins; they cluster in Pro- and Gln-rich regions, which are also more resistant to gastrointestinal digestion. Specific Gln residues in these epitopes are particularly prone to deamidation by TG2, especially as part of the sequence Gln-Xaa-Pro. This clustering of epitopes results in polyvalent peptide fragments that appear to be particularly immunogenic. For example, a 33-mer fragment of an α-gliadin, LQLQPFPQPQLPYPQPQLPYPQPQLPYPQPQPF (αG-33), which is naturally formed by digestion with gastric and pancreatic enzymes and which is resistant to further degradation by brush border enzymes, contains 6 partly overlapping copies of three different T cell epitopes (DQ2-α-I, DQ2-α-II and DQ2-α-III). It is an excellent substrate for TG2, and is recognized by intestinal T cell lines from all Celiac Sprue patients much more effectively than shorter peptides covering single epitopes.

The digestive resistance of gluten peptides and their DQ2 (or DQ8) mediated presentation to disease-specific T cells is clearly central to the pathogenesis of Celiac Sprue. Recent studies have indicated that the Pro-rich immunogenic α-gliadin epitopes, including the αG-33 fragment, can be rapidly cleaved by prolyl endopeptidases (PEPs) into short sequences that either lack T cell stimulatory capacity or can be further broken down by the peptidases of the intestinal brush border membrane. This suggests a potentially powerful therapeutic approach towards detoxification of gluten ingested by a Celiac Sprue patient. However, in order to be therapeutically useful, PEP must also accelerate the breakdown of Pro- and Gln-rich gluten proteins other than α-gliadin. Food-grade gluten is an extremely complex protein mixture that consists of hundreds of distinct (but related) gliadin and glutenin polypeptides. Approximately 60% of the gliadin proteins are α-gliadins, 30% are γ-gliadins and 10% are ω-gliadins. From these proteins, several epitopes have been identified, as summarized in Table 1. Here we demonstrate that PEP, in combination with gastric and pancreatic enzymes as well as brush border membrane enzymes, is able to reduce the immune response of patient derived intestinal T cells to less than 2% of the response induced by positive controls in most cases. In addition, LC-MS-MS analysis supports and partially explains these results at a chemical level.

Materials and Methods

Materials-All enzymes were purchased from Sigma (St. Louis, Mo.) except for Pepsin, which was obtained from American Laboratories, Inc. (Omaha, Nebr.) and Trypsin+ Chymotrypsin, which was purchased from Enzyme Development Co. (New York, N.Y.). The specific activities of all enzymes were tested using standard chromogenic assays prior to use, and were found to be: Pepsin: 4000 U/mg; Trypsin: 2000 USP/mg; Chymotrypsin: 800 USP/mg; Elastase: 5 U/mg; Carboxypeptidase A: 30 U/mg. Wheat flour used for gluten preparation was purchased in bulk from Bob's Red Mill (Milwaukie, Oreg.). All other reagents were food or reagent grade. Substrates for the chromogenic assays were purchased from Sigma except for Z-Glu-Pro-p-nitroanilide, which was purchased from Bachem (Basel, Switzerland). 96-Well plates were purchased from VWR. All UV/Vis measurements were performed on a Spectramax 384 Plus (Molecular Devices, Mountain View, Calif.).

Activity assays—Pepsin: 300 μL 2.5% Hemoglobin and 75 μL 0.3 M HCl were mixed and incubated for 10' at 37° C., then added to 75 μL pepsin solution (0.1 mg/ml in 0.01 M HCl, pH=2.0). The samples were incubated for 0', 10' and 20' at 37° C. (3 samples), and the reaction was stopped by addition of 750 μL 5% Trichloroacetic acid (TCA), and incubated 5' at 37° C. For the 0' samples, the TCA was added before the hemoglobin. Samples were centrifuged for 10' at 13400×g. The absorption was recorded at 280 nm. One unit renders TCA soluble absorption of 0.001 at 280 nm per min at 37° C. from a denatured hemoglobin substrate.

Trypsin: 870 µL 46 mM Tris-HCl, 11.5 mM $CaCl_2$, pH 8.1 and 100 µL 10 mM N-α-p-Tosyl-L-Arginine methyl ester (TAME) were mixed and incubated at room temperature for 10'. 5 µL Trypsin (1 mg/ml) were added and the absorption at 247 nm was recorded for 2', every 10". Unit definition: One unit hydrolyzes 1 µmol of TAME per min at pH 8.2 and 25° C. Extinction coefficient 0.18 $cm^2$/µmol at 247 nm. 1 TAME unit=19.2 USP units.

Chymotrypsin: 750 µL 80 mM Tris-HCl, 100 mM $CaCl_2$, pH 7.8 and 700 µL 1.07 mM BTEE (in Water/MeOH 1:1) were mixed and incubated at room temperature for 10'. 5 µL Chymotrypsin (1 mg/ml) were added and the absorption at 256 nm was recorded for 2', every 10". One unit hydrolyzes 1 µmol of BTEE per min at pH 7.8 and 25° C. Extinction coefficient 0.964 $cm^2$/µmol at 256 nm. 1 BTEE unit=29.55 USP units.

Elastase: 935 µL 0.1 M Tris (pH 8.0) and 65 µL of Succinyl-$Ala_3$-p-Nitro anilide (4.4 mM in 0.1 M Tris, pH 8.0) were mixed and incubated at room temperature for 10'. 5 µL Elastase (0.2 mg/ml) were added and the absorption at 410 nm was recorded for 2', every 10". One unit hydrolyzes 1 µmol of Succinyl-$Ala_3$-p-Nitro anilide per min at pH 8.0 and 25° C. Extinction coefficient 8.8 $cm^2$/µmol at 410 nm. 1 TAME unit=19.2 USP units.

Carboxypeptidase A: 995 µL 1.0 mM Hippuryl-L-Phe in 25 mM Tris and 500 mM NaCl, pH 7.5 was mixed with 5 µL Carboxypeptidase A (0.2 mg/ml). Absorption at 254 nm was recorded for 2', every 10". One unit hydrolyzes 1 µmol of Hippuryl-L-Phe per min at pH 7.5 and 25° C. Extinction coefficient 0.36 $cm^2$/µmol at 254 nm. PEP: To 10 µL Z-Gly-Pro-p-Nitroanilide 16.8 mg/ml in dioxane were added 70 µL dioxane, 120 µL water and 800 µL PBS buffer. This substrate solution was incubated at 37° C. for 10'; then 0.2-2 µL PEP were added and the absorption at 410 nm was recorded for 2', every 10". One unit hydrolyzes 1 µmol of Z-Gly-Pro-p-Nitroanilide per min at pH 7.5 and 37° C. Extinction coefficient 8.8 $cm^2$/µmol at 410 nm.

DPP IV from rat brush border membrane (BBM): To 66 µL of Gly-Pro-p-nitroanilide (15.2 mM in 0.1 M Tris-HCl, pH=8.0), 935 µL of 0.1 M Tris-HCl, pH=8.0 were added. This substrate solution was incubated at 30° C. for 10'; then 5-10 µL of rat BBM (1 mg/ml) were added and the absorption at 410 nm was recorded for 2', every 10". One unit hydrolyzes 1 µmol of Gly-Pro-p-Nitroanilide per min at pH 8.0 and 30° C. Extinction coefficient 8.8 $cm^2$/µmol at 410 nm.

APN from rat brush border membrane: To 10 µL of Leu-p-nitroanilide (100 mM in DMSO), 990 µL of 0.1 M Tris-HCl, pH=8.0 were added. This substrate solution was incubated at 30° C. for 10'; then 5-10 µL of rat BBM (1 mg/ml) were added and the absorption at 410 nm was recorded for 2', every 10". One unit hydrolyzes 1 µmol of Leu-p-nitroanilide per min at pH 8.0 and 30° C. Extinction coefficient 8.8 $cm^2$/µmol at 410 nm.

Isolation of rat brush border membrane—a Sprague-Dawley rat (male or female) was anesthetized using ketamine and 10 cm of its jejunum was removed surgically and stored on ice immediately; the rat was then killed by exposure to $CO_2$ and subsequent cervical dislocation. The jejunum was washed with 0.9% NaCl, 1 mM DTT and subsequently cut open longitudinally, and the mucosa was scraped off carefully. The mucosa was homogenized in a Dounce homogenizer in 5 mM EDTA and 5 mM histidine-imidazole, pH 7.4, and centrifuged at 55,000×g for 20 min at 4° C. 15 ml of 0.25 M sorbitol, 12.5 mM NaCl, 0.5 mM EDTA and 5 mM histidine-imidazole, pH 7.4 was added to the pellet, which was homogenized again, diluted to 25 ml and centrifuged at 1,400×g for 10 min at 4° C. To the pellet, 5 ml of 50 mM mannitol in 2 mM Tris-HCl, pH 7.1 were added, and the solid was homogenized in a Polytron homogenizer. The homogenate was diluted to 10 ml, $CaCl_2$ was added to a final concentration of 10 mM and the suspension was stirred for 30 min at 4° C. Subsequently, it was centrifuged at 2,000×g for 10 min at 4° C.; the supernatant was collected and centrifuged for 20 min at 20,000×g at 4° C. The resulting pellet was re-suspended in PBS, pH 7.1. Activity of the preparation was confirmed by analysis of APN and DPP IV activities.

Gluten treatment with gastric and pancreatic enzymes—Wheat gluten flour (3.0 g) was added to 100 ml of water with addition of HCl to achieve a stable suspension at pH 2.0. Pepsin (Pepsin NF powder, 1:10000, 60 mg) was mixed in to the gluten suspension and the gluten-pepsin mixture was shaken constantly at 37° C. for 2 h. After the pepsin treatment had been completed, 350 mg of $Na_2HPO_4$ were added and the pH adjusted to 7.9 by addition of 0.1 M NaOH. Trypsin/Chymotrypsin (38 mg) were added and the mixture was shaken again at 37° C. for 2 h and then heated to >95° C. for 10 min. After cooling to room temperature, 74 µL of the mixture was treated with Elastase (20 µL, 1 mg/ml) and the mixture was diluted to 1.7 mg/ml using PBS buffer, pH=7.5. The mixture was maintained at 37° C. After 2 h the digested gluten suspension was heated to 95° C. for 10 minutes and cooled to room temperature. After this, 20 µL of Carboxypeptidase A were added and incubated for 2 h at 37° C., and subsequently heat deactivated.

Prolyl endopeptidase (PEP) and Brush Border Membrane (BBM) treatment—Recombinant PEP (Sp. Act ~40 U/mg) was added at a ratio of 200 mU/mg of the PTC-digested gluten substrate, and incubated at 37° C. for 15 min to 1 h and then heat de-activated, depending on the sample. Subsequently BBM (65 mU (DPP IV activity)/mg substrate) was added and the mixture was incubated for 1 h and heat de-activated. Control samples contained PEP and BBM buffer solutions without the enzymes.

RP-HPLC—Analyses were performed on a system consisting of Rainin Dynamax SD-200 pumps running at 1 ml/min, a Varian 340 UV detector set at 215 nm and a Varian Prostar 430 Autosampler. Solvent A was $H_2O$ with 0.1% TFA and solvent B was acetonitrile with 0.1% TFA; separation was performed on a 4.6×150 mm reverse phase C-18 protein & peptide column (Vydac, Hesperia, Calif., USA). Samples were centrifuged for 10 min at 13,400×g, prior to injection.

HPLC-MS—Separations were performed on a Surveyor HPLC system (ThermoFinnigan, San Jose, Calif., USA). Solvent A was $H_2O$ with 0.1% formic acid and 0.025% TFA; solvent B was acetonitrile with 0.085% formic acid and 0.022% TFA. Samples were chromatographed on a 2.0×150 mm reverse phase C18 column (Vydac, Hesperia, Calif., USA) at a flow rate of 200 uL/min, using a gradient of 5-35% B over 30 min. The outlet of the column was connected directly to an LCQ quadrupole ion trap (ThermoFinnigan, San Jose, Calif., USA) mass spectrometer equipped with an electrospray ion source operating in positive ion mode. The sheath gas was set to 60 (arbitrary units), spray voltage to 4.5 kV, and capillary temperature to 200° C. The system acquires full MS, zoom scan, and MS/MS spectra in an automatic data dependent mode.

Data was processed using Sequest Browser software. Detected ions and fragments were searched against all sequences in the Entrez Protein database of the National Center for BioInformatics (NCBI) that responded to the search term "*Triticum*" (>2000 protein sequences). Sequences with a cross correlation value below 1.5 were rejected; the remaining sequences were searched for epitopes sequences listed in Table 1.

TABLE 1

Epitopes recognized by intestinal T cells of Celiac Sprue patients. These sequences were used to search for epitope-containing peptides in alternatively treated gluten samples.

| T cell epitope | Source | | | Native sequence of 9-mer core region of epitope[4] | T-cell clone | in this study |
|---|---|---|---|---|---|---|
| α-I (Var1) | α-gliadin, recombinant[1] | SEQ ID NO:11 | PFPQPQLPY | Crystal[5] | TCC 387 E9 | |
| α-III (Var2 of α-I) | α-gliadin, recombinant[1] | SEQ ID NO:13 | PYPQPQLPY | TCC[6] | TCC 370 E3.19 | |
| α-II | α-gliadin, recombinant[1] | SEQ ID NO:14 | PQPQLPYPQ | DQ-TCC[7] | TCC 4301.135 | |
| Glia-α20 | α-gliadin, peptide[2] | SEQ ID NO:15 | FRPQQPYPQ | TCC[6] | | |
| γ-I | γ-gliadin, natural[3] | SEQ ID NO:16 | PQQSFPQQQ | DQ-TCC[7] | TCC 423.1.3.8 | |
| γ-II (Glia-γ30) | γ-gliadin, natural[3] | SEQ ID NO:17 | IQPQQPAQL | TCC[6] | TCC 430.1.41 | |
| γ-III | γ-gliadin, recombinant[1] | SEQ ID NO:18 | QQPQQPYPQ | TCC[6] | TCC 430.1.134 | |
| γ-IV | γ-gliadin, recombinant[1] | SEQ ID NO:19 | SQPQQQFPQ | TCC[6] | TCC 430.1.112 | |
| γ-VI | γ-gliadin, recombinant[1] | SEQ ID NO:20 | QQPFPQQPQ | TCC[6] | TCC 387.3 | |
| Glia-γ2 | γ-gliadin, unknown | SEQ ID NO:21 | PYPQQPQQP | | | |
| Glu-5 (Var1) | Not defined, natural[3] | SEQ ID NO:22 | QIPQQPQQF | TCC[6] | | |
| Glu-5 (Var2) | Not defined, natural[3] | SEQ ID NO:23 | QLPQQPQQF | TCC[6] | | |
| Glt-17 (Var1) | LMW-glutenin, peptide[2] | SEQ ID NO:24 | PFSQQQQPV | TCC[6] | | |
| Glt-17 (Var2) | LMW-glutenin, peptide[2] | SEQ ID NO:25 | PFSQQQQPI | TCC[6] | | |

[1]Identified from fragments of recombinant gliadin protein digests.
[2]Identified from panels of synthetic peptides.
[3]Identified from fragments of natural gliadin or gluten protein digests.
[4]Core 9-mer region interacting with DQ2 is shown. T cells usually require additional flanking residues for recognition. Glutamine residues deamidated by tissue transglutaminase are underlined.
[5]Defined by the crystal structure of the peptide DQ2 complex.
[6]Register defined from minimal fragment recognized by specific T cell clones and binding motif of DQ2.
[7]Register defined from minimal fragment recognized by specific T cell clones and DQ2 binding assay.

T cell assays—The generation of polyclonal gluten-specific T cell lines derived from ex vivo gluten challenged small intestinal biopsy specimens of adult Celiac Sprue patients have been described elsewhere. For this study 14 different intestinal T cell lines derived from 13 DQ2+celiac patients were selected based on two basic criteria; effective recognition of TG2-treated digests of gluten and significant responses to at least two different gluten epitopes (Table 2). The generation of intestinal T cell clones and the epitope specificity of these clones, except TCC 387.3, has been described elsewhere (10). The TCC 387.3 recognizes a TG2-dependent epitope, defined as γ-VI that is contained within residues 62-72 (PQQPFPQQPQQ) of recombinant γ-5 gliadin. The freeze-dried, proteolyzed gluten samples were dissolved in PBS with 2 mM CaCl$_2$ and treated with 150 µg/ml human recombinant TG2 (14) or, in some experiments 200 µg/ml guinea pig transglutaminase (Sigma T-5398), for 2 hours at 37° C. The TG2-treated samples were incubated overnight in triplicates on U-bottomed 96 well plates with 75 000 cells per well of DQ2 homozygous, irradiated (75 Gy) EBV-transformed B-lymphoblastoid cell lines in a volume of 100 µl 15% pooled, inactivated human serum and RPMI1640. After the incubation 50 µl of freshly thawed T cells (1×10$^6$ cells/ml) were added to each well. The proliferation in the wells was evaluated by $^3$H thymidine incorporation from 48-72 hours after the addition of the T cells.

TABLE 2

Epitope recognition pattern of celiac lesion derived polyclonal T cell lines used in this study. Each intestinal T cell line was tested with DQ2+ APC using 5 µM TG2-treated peptide, and the response was evaluated by $^3$H thymidine incorporation.

| T cell line | Response to TG2-treated gluten peptides | | | | | | |
|---|---|---|---|---|---|---|---|
| | αG-33[1] | α-I[1] | α-II | γ-I | γ-II | γ-III and γ-VI | Glu-5 |
| 421.1.4 | ++ | − | + | − | + | + | − |
| 422.4.2 | ++ | + | ++ | − | − | − | − |
| 432.2.1 | ++ | − | ++ | + | − | − | − |
| 437.1.1 | ++ | − | + | − | − | − | − |
| 437.1.3 | ++ | + | + | + | − | − | − |
| 446.1.3 | ++ | + | ++ | − | ++ | − | + |
| 451.1.1 | ++ | − | + | − | ++ | − | − |
| 461.1.4 | + | − | + | − | − | + | − |
| 482.1.4 | ++ | − | + | − | − | − | − |
| 488.3.1 | ++ | + | ++ | − | − | + | − |
| 491.1.3 | ++ | + | ++ | + | − | − | + |
| 494.1.1 | ++ | + | ++ | − | − | ++ | − |
| 496.1.2 | ++ | ++ | + | − | ++ | + | − |
| 502.1.2 | ++ | ++ | + | − | − | + | − |

[1]The sequences of the native peptides treated with TG2 were as follows; αG-33, LQLQPFPQPQLPYPQPQLPYPQPQLPYPQPQPF; α-I, QLQPF-PQPQLPY; α-II, PQPQLPYPQPQLPY; γ-I, QPQQPQQSFPQQQRP; γ-II, GIIQPQQPAQL; γ-III and γ-VI, LQPQQPFPQQPQQPYPQQPQ; Glu-5, QQxSQPxPQQQQxPQQPQQF (where x is I or L, reference Vader, Gastroenterology 2002)
−; no response,
+; Stimulatory index (SI; T + APC + TG2-treated peptide divided by T + APC) of 3-10 and
++; SI above 10.

Results

Proteolysis of Gluten and Reverse-Phase High-Performance Liquid Chromatography (RP-HPLC) Analysis. Wheat gluten flour was proteolyzed with pepsin, followed by pancreatic proteases (trypsin, chymotrypsin, elastase and carboxypeptidase A), followed by PEP (or vehicle), and eventually BBM (or vehicle). The overall proteolytic protocols are as described in the Materials and Methods section, and summarized FIG. 1. Samples 1 to 7 were prepared as described in Table 3.

TABLE 3

| Epitope | Sample |   |   |   |   |   |   |
|---|---|---|---|---|---|---|---|
|  | 1 | 2 | 3 | 4 | 5 | 6 | 7 |
| Duration PEP treatment (min) | no PEP | 15 | 60 | no PEP | 15 | 60 | 0 |
| Duration BBM treatment (min) | no BBM | no BBM | no BBM | 60 | 60 | 60 | 0 |

Treatment scheme of Pepsin/Trypsin/Chymotrypsin/Elastase/Carboxypeptidase A (PTCEC) treated whole gluten.

Figure 2:
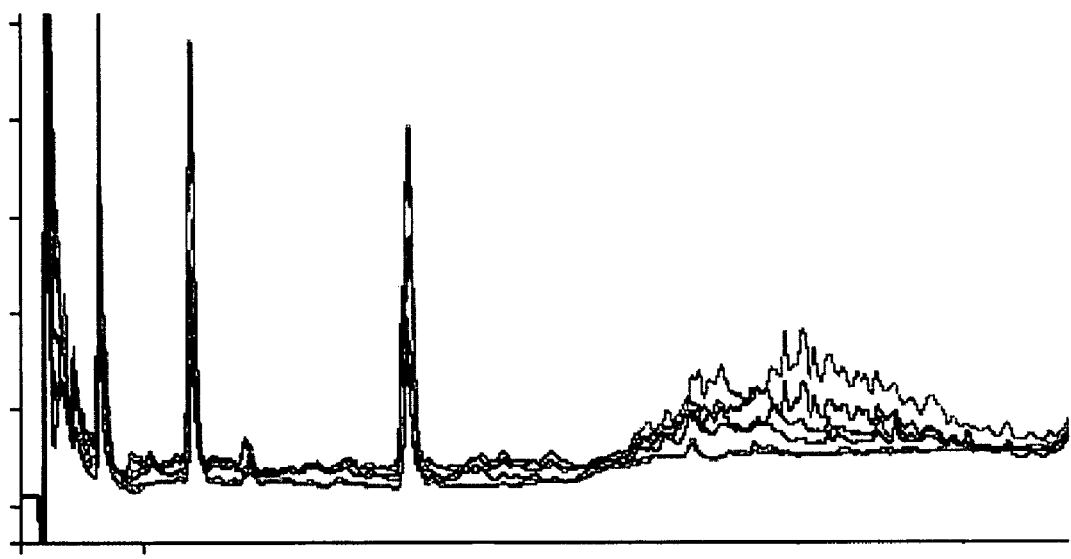

The gluten samples 1-7 were initially analyzed using RP-HPLC (FIG. 2). Due to the complexity of the mixtures analyzed, individual peaks could not be monitored; most of the observed peaks are likely to represent mixtures of peptides. As expected, the HPLC traces of the samples 1 and 7 (controls, digestion by gastric and pancreatic proteases only) showed no qualitative difference. Treatment of samples with PEP only (samples 2 and 3) resulted in attenuation of late-eluting peptide peaks (>23 min); based on earlier experience with gluten peptides of varying length and sequence, these peaks were presumed to correspond to longer peptides. Treatment with BBM in all cases led to almost complete decomposition of all peaks eluting after 15 min, together with a strong increase of peaks eluting after 3, 7, and 13 min.

Liquid Chromatography Coupled Tandem Mass Spectrometry (LC-MS/MS)

Figure 3:
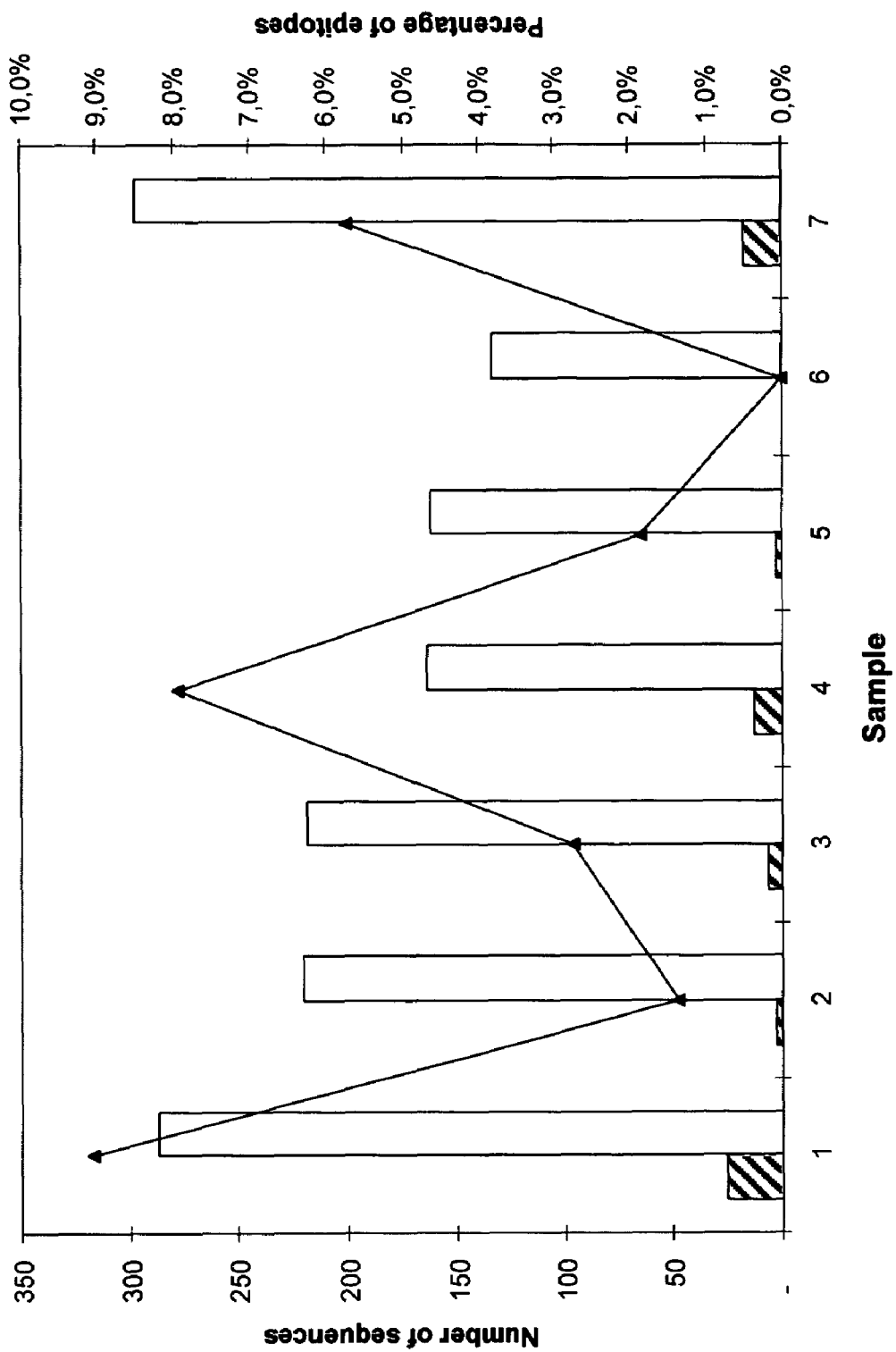

Overall analysis. The samples were separated on a reverse-phase column and analyzed in a MS/MS detector with coupled database search capabilities using the program Sequest. The library employed for the search consisted of all wheat family (Triticum) sequences deposited in the NCBI Entrez Protein database. The number of distinct peptides with lengths between 4 and 55 AA in each gluten sample varied between 133 (sample 6) to 314 (sample 7) (FIG. 3). Overall, 1549 sequences with a cross-correlation>1.5 were identified, including duplicates. When the cross-correlation, which serves as a measure for the reliability of an identified sequence, was lowered to 1.0, the number of distinct peptides increased from 314 to 444 in sample 7. If the cross-correlation was increased to 2.0, the number decreased from 314 to 162 for the same sample.

Length distribution of identified sequences xC=1.5. The average length of the 1549

| Epitope | Sample 1 | Sample 2 | Sample 3 | Sample 4 | Sample 5 | Sample 6 | Sample 7 |
|---|---|---|---|---|---|---|---|
| α-I | 2 | — | — | 3 | — | — | 1 |
| α-II | 2 | — | — | 1 | — | — | 1 |
| α-III | 2 | — | — | 1 | — | — | — |
| Glia-α20 | — | — | — | 1 | — | — | — |
| γ-I | — | — | — | — | — | — | — |
| γ-II | 2 | — | — | — | — | — | 2 |
| γ-III | — | — | — | — | — | — | — |
| γ-IV | — | — | — | — | — | — | — |
| γ-VI | 12 | 3 | 4 | 7 | 3 | — | 6 |
| Glia-γ2 | 2 | — | — | — | — | — | — |
| Glu-5 (Var 1) | — | — | — | — | — | — | — |
| Glu-5 (Var 2) | — | — | — | — | — | — | — |
| Glt-17 (Var 1) | 4 | — | 2 | — | — | — | 7 |
| Glt-17 (Var 2) | — | — | — | — | — | — | — |
| Total | 26 | 3 | 6 | 13 | 3 | — | 17 | identified sequences identified in samples 1 through 7 was 20.3 residues. No clear trend could be deduced from the data; the minimum average length was 17.3 residues (sample 2), whereas the maximum average length was 26.0 residues (sample 7).

Abundance of epitope-containing peptides. The amino acid sequences of the proteolytic fragments identified in samples 1-7 were screened for core DQ2-binding epitopes (9 residues) corresponding to the majority of (DQ2 restricted) T cell stimulatory gluten peptides identified to date (see Table 1). In total, 68 distinct epitope containing peptides were identified (Table 4 and Supplemental Table 1). Except for the γ-VI epitope, nearly all of the epitope containing peptides were present in non-PEP treated samples. The percentage of the epitope-bearing peptides in each sample is also shown in FIG. 3. As can be seen, there is a pronounced reduction in the prevalence of epitope-bearing peptides in samples treated with PEP.

Table 4

Number of Distinct Peptides in the Individual Samples that Harbor the 9-mer Core Regions of T Cell Epitopes (Table 1). The Sequences of These Peptides are Given in Supplemental Table 1.

TABLE 5

| Entry | Epitope | Sequence | Sample # | Epitope containing sequence |
|---|---|---|---|---|
| 1a | α-I | SEQ ID NO:11 PFPQPQLPY | 1 (2x) | (SEQ ID NO:32) QPFPQPQLPYPQPQL*PYPQ PQLPYPQPQP* |
| 1b | α-II | SEQ ID NO:14 PQPQLPYPQ | 1 (2x) | (SEQ ID NO:33) QPFPQPQLPYPQPQL*PYPQ PQLPYPQPQP* |
| 1c | α-III | SEQ ID NO:13 PYPQPQLPY | 1 (2x) | (SEQ ID NO:34) QPFPQPQLPYPQPQL*PYPQ PQLPYPQPQP* |
| 2a | α-I | SEQ ID NO:11 PFPQPQLPY | 4 | (SEQ ID NO:35) PFPQPQLPYPQPQL*PYPQP QLPYPQPQP* |
| 2b | α-II | SEQ ID NO:14 PQPQLPYPQ | 4 | (SEQ ID NO:36) PFPQPQLPYPQPQL*PYPQP QLPYPQPQP* |
| 2c | α-III | SEQ ID NO:13 PYPQPQLPY | 4 | (SEQ ID NO:37) PFPQPQLPYPQPQL*PYPQP QLPYPQPQP* |
| 3 | α-G33 | Not found |  | (SEQ ID NO:38) LQLQPFPQPQLPYPQPQL*P YPQPQLPYPQPQPF* |
| 4 | α-I | SEQ ID NO:11 PFPQPQLPY | 4 | (SEQ ID NO:39) QPFPQPQLPYPQPQPFRPQ |
| 5a | α-I | SEQ ID NO:11 PFPQPQLPY | 4 | (SEQ ID NO:40) PFPQPQLPYLQPQPFRPQQ PYPQPQP |
| 5b | Glia-α20 | SEQ ID NO:20 FRPQQPYPQ | 4 | (SEQ ID NO:41) PFPQPQLPYLQPQPFRPQQ PYPQPQP |
| 6a | α-I | SEQ ID NO:11 PFPQPQLPY | 7 | (SEQ ID NO:42) QPFPQPQLPYPQPQPFRPQ Q |

TABLE 5-continued

| Entry | Epitope | Sequence | Sample # | Epitope containing sequence |
|---|---|---|---|---|
| 6b | α-II | SEQ ID NO:14 QPFPQPQLPYPQPQPFRPQ PQPQLPYPQ | 7 | (SEQ ID NO:43) QPFPQPQLPYPQPQPFRPQ Q |

TABLE 6

| Entry | Epitope | Sequence | Sample # | Epitope containing sequence |
|---|---|---|---|---|
| 1a | γ-II | SEQ ID NO:17 IQPQQPAQL | 1 (2x) | (SEQ ID NO:44) PLFQLVQGQGIIQPQQPAQ LEVIRSLVLG |
| 1b | γ-II | SEQ ID NO:17 IQPQQPAQL | 7 (2x) | (SEQ ID NO:45) PLFQLVQGQGIIQPQQPAQ LEVIRSLVLG |
| 2 | γ-VI | SEQ ID NO:20 QQPFPQQPQ | 1 (2x) | (SEQ ID NO:46) QVPQPQQPQQPFLQPQQPF PQQPQQPFPQTQQPQQPFP QQP |
| 3 | γ-VI | SEQ ID NO:20 QQPFPQQPQ | 1 | (SEQ ID NO:47) FLQPQQPFPQQPQQPFPQT QQPQQPFPQQP |
| 4a | γ-VI | SEQ ID NO:20 QQPFPQQPQ | 1 | (SEQ ID NO:48) PQPQQPQQPFLQPQQPFPQ QPQQP |
| 4b | γ-VI | SEQ ID NO:20 QQPFPQQPQ | 7 | (SEQ ID NO:49) PQPQQPQQPFLQPQQPFPQ QPQQP |
| 5 | γ-VI | SEQ ID NO:20 QQPFPQQPQ | 7 | (SEQ ID NO:50) PQQPQQPFLQPQQPFPQQP QQP |
| 6 | γ-VI | SEQ ID NO:20 QQPFPQQPQ | 4 | (SEQ ID NO:51) PFLQPQQPFPQQPQQPFP |
| 7a | γ-VI | SEQ ID NO:20 QQPFPQQPQ | 1 | (SEQ ID NO:52) LQPQQPFPQQPQQPFPQ |
| 7b | γ-VI | SEQ ID NO:20 QQPFPQQPQ | 7 | (SEQ ID NO:53) LQPQQPFPQQPQQPFPQ |
| 8 | γ-VI | SEQ ID NO:20 QQPFPQQPQ | 1 | (SEQ ID NO:54) QQSEQIIPQQLQQPFPLQP QQPFPQQPQQPFP |
| 9 | γ-VI | SEQ ID NO:20 QQPFPQQPQ | 2 | (SEQ ID NO:55) QPFPLQPQQPFPQQPQQPF PQPQQPIPVQ |
| 10 | γ-VI | SEQ ID NO:20 QQPFPQQPQ | 3 | (SEQ ID NO:56) QPFPLQPQQPFPQQPQQPF PQPQQPIP |
| 11 | γ-VI | SEQ ID NO:20 QQPFPQQPQ | 3 | (SEQ ID NO:57) PQQPQQPFPQTQQPQQPFP QQPQQPFPQTQQPQQPFPQ QP |
| 12 | γ-VI | SEQ ID NO:20 QQPFPQQPQ | 3 | (SEQ ID NO:58) TQQPQQPFPQQPPFPQTQQ PQQPFPQQPQQPFPQ |
| 13 | γ-VI | SEQ ID NO:20 QQPFPQQPQ | 4 (2x) | (SEQ ID NO:59) TQQPQQPFPQQPQQPFPQT Q |
| 14 | γ-VI | SEQ ID NO:20 QQPFPQQPQ | 1 | (SEQ ID NO:60) FPQTQQPQQPFPQQPQQPF P |
| 15a | γ-VI | SEQ ID NO:20 QQPFPQQPQ | 1 (2x) | (SEQ ID NO:61) TQQPQQPFPQQPQQPFPQ |
| 15b | γ-VI | SEQ ID NO:20 QQPFPQQPQ | 4 | (SEQ ID NO:62) TQQPQQPFPQQPQQPFPQ |
| 15c | γ-VI | SEQ ID NO:20 QQPFPQQPQ | 7 (2x) | (SEQ ID NO:63) TQQPQQPFPQQPQQPFPQ |
| 16 | γ-VI | SEQ ID NO:20 QQPFPQQPQ | 4 | (SEQ ID NO:64) TQQPQQPFPQQPQQPFP |
| 17 | γ-VI | SEQ ID NO:20 QQPFPQQPQ | 3 | (SEQ ID NO:65) PQQLFPELQQPIPQQPQQP FPLQPQQPFPQQPQQPFPQ QP |
| 18 | γ-VI | SEQ ID NO:20 QQPFPQQPQ | 1 | (SEQ ID NO:66) FPELQQPIPQQPQQPFPLQ PQQPFPQQPQQP |
| 19 | γ-VI | SEQ ID NO:20 QQPFPQQPQ | 1 | (SEQ ID NO:67) PQQPFPQQPQQPVPQQSQQ PFPQTQQPQQ |
| 20 | γ-VI | SEQ ID NO:20 QQPFPQQPQ | 1 | (SEQ ID NO:68) QPQQPTPIQPQQPFPQQPQ QPQQPFP |
| 21a | γ-VI | SEQ ID NO:20 QQPFPQQPQ | 2 | (SEQ ID NO:69) QPFPQQSQQPFPQQPQQS |
| 21b | γ-VI | SEQ ID NO:20 QQPFPQQPQ | 4 (2x) | (SEQ ID NO:70) QPFPQQSQQPFPQQPQQS |
| 21c | γ-VI | SEQ ID NO:20 QQPFPQQPQ | 5 (2x) | (SEQ ID NO:71) QPFPQQSQQPFPQQPQQS |
| 22 | γ-VI | SEQ ID NO:20 QQPFPQQPQ | 2 | (SEQ ID NO:72) QQSQQPFPQQPQQS |
| 23 | γ-VI | SEQ ID NO:20 QQPFPQQPQ | 5 | (SEQ ID NO:73) PQQPQQPFPQQPQQP |
| 24 | γ-VI | SEQ ID NO:20 QQPFPQQPQ | 7 | (SEQ ID NO:74) QPQQPFPQQPQ |
| 25 | Glia-γ2 | SEQ ID NO:21 PYPQQPQQP | 1 (2X) | (SEQ ID NO:75) PRQPYPQQPQQP |

TABLE 7

| Entry | Epitope | Sequence | Sample # | Epitope containing sequence |
|---|---|---|---|---|
| 1 | Glt-17 (Var 1) | SEQ ID NO:24 PFSQQQPV | 1 (2x) | (SEQ ID NO:76) SQQQPPFSQQQPPFSQQQ QPV |

TABLE 7-continued

| Entry | Epitope | Sequence | Sample # | Epitope containing sequence |
|---|---|---|---|---|
| 2 | Glt-17 (Var 1) | SEQ ID NO:24 PFSQQQQPV | 7 (2x) | (SEQ ID NO:77) SQQQQPPFSQQQPPFSQQQ QPV |
| 3 | Glt-17 (Var 1) | SEQ ID NO:24 PFSQQQQPV | 1 | (SEQ ID NO:78) SQQQPPFSQQQQPV |
| 4 | Glt-17 (Var 1) | SEQ ID NO:24 PFSQQQQPV | 7 | (SEQ ID NO:79) SQQQPPFSQQQQPV |
| 5 | Glt-17 (Var 1) | SEQ ID NO:24 PFSQQQQPV | 1 | (SEQ ID NO:80) SQQQLPPFSQQQPPFSQQQ QPV |
| 6 | Glt-17 (Var 1) | SEQ ID NO:24 PFSQQQQPV | 7 (2x) | (SEQ ID NO:81) SQQQLPPFSQQQPPFSQQQ QPV |
| 7 | Glt-17 (Var 1) | SEQ ID NO:24 PFSQQQQPV | 3 | (SEQ ID NO:82) PPFSQQQQPVLPQQPPFSQ QQQQQQQPPFSQQQQPV |
| 8 | Glt-17 (Var 1) | SEQ ID NO:24 PFSQQQQPV | 7 | (SEQ ID NO:83) VLPQQPPFSQQQQPVLPPQ QSP |
| 9 | Glt-17 (Var 1) | SEQ ID NO:24 PFSQQQQPV | 7 | (SEQ ID NO:84) FSQQQLPPFSQQLPPFSQQ QQQVLPQQPPFSQQQQPV |
| 10 | Glt-17 (Var 1) | SEQ ID NO:24 PFSQQQQPV | 3 | (SEQ ID NO:85) FSQQQLPPFSQQLPPFSQQ QQQVLPQQPPFSQQQQPV |

Origins and sequences of epitope-containing peptides. The origins of the 68 epitope-containing peptides in samples 1-7 are summarized in Table 4, and their individual sequences are detailed in Tables 5, 6 and 7. Notably, although a majority of gluten proteins in the Entrez database are γ-gliadin and glutenin sequences rather than α- or ω-gliadins, α-gliadin peptides comprise 32% of all identified epitope-bearing peptides.

α-gliadin epitopes. Whereas each of the three known α-gliadin epitopes (α-I, α-II and α-III) were found in untreated and BBM treated gluten (samples 1, 4 and 7), PEP treatment (samples 2, 3, 5 and 6) led to the elimination of all α-gliadin epitope-bearing peptides (Table 4). All α-gliadin epitopes were found to occur in two closely related families of gluten peptides (Table 5; entries 1-2 and entries 4-6); the first of these families is closely related to the previously identified 33-mer αG-33 (Table 5; entry 3).

γ-gliadin epitopes. Although the γ-VI epitope was identified in all samples except in sample 6, there was a tendency towards fewer γ-VI epitope-bearing peptides in the PEP-treated samples (Table 4 and Table 6). Thus, this epitope appears to be somewhat resistant to cleavage by the *F. meningosepticum* PEP. The 9-mer core region of this epitope was identified in at least nine different gluten peptides. This is likely a major factor contributing to the many hits observed for this epitope. The γ-II epitope was found in sample 1 and 7 and Glia-γ2 was found in sample 1 (Table 4 and Table 6).

Other epitopes. Epitope Glt-17 was found in samples 1, 3 and 7, and occurs in the context of multiple peptides (Table 4 and Table 7).

T Cell Assays—Polyclonal T Cell Lines

T cell assays were performed on 14 polyclonal cell lines derived from small intestinal biopsies of Celiac Sprue patients as well as 8 intestinal T cell clones that recognize distinct epitopes. The intestinal T cell lines were selected on basis of their responses to whole gluten and a broad response pattern to selected gluten epitopes (Tables 1 and 2). As was expected from previous experience, all T cell lines displayed vigorous dose-dependent responses to the TG2-treated gluten (sample 1) (FIGS. 4 and 5), but hardly responded to untreated gluten (data not shown). Therefore, all samples were treated with TG2, and tested at four different dilutions. From previous studies we also knew that 250 µg/ml TG2-treated gluten would be sufficient to obtain near maximal T cell proliferation; this value was thus chosen as the highest test concentration for all samples. FIG. 4 shows the responses of 14 polyclonal T cell lines to 250 µg/ml of alternatively prepared gluten samples. BBM treatment alone can attenuate the T cell response (sample 4 versus sample 1), as illustrated by the T cell lines TCL 421.1.4 and 451.1.1. However, this effect is modest compared to the dramatic decline in T cell response seen after 15', and especially 60' of PEP treatment (samples 2 and 3). Notably, in many cases the combined effects of BBM and PEP appear to be synergistic rather than simply additive. FIG. 5 shows the dose-dependence of responses to samples 1-6 in six of the T cell lines. A similar picture was obtained with the remaining eight T cell lines.

To quantify the effects of PEP and BBM treatment of gluten on its ability to induce proliferation of different T cell lines, the amounts of radioactivity incorporated in samples 3 (PEP alone), 4 (BBM alone) and 6 (PEP+BBM) were expressed as a percentage of the radioactivity incorporated in sample 1 (no PEP or BBM) (Table 5). In cases where the T cell response was less than 2% of the response to sample 1, the sample was considered as "completely detoxified". A sample that retained between 2% and 20% of the T cell stimulatory capacity were considered as "partially detoxified", while all others were "not detoxified". Although this categorization is somewhat arbitrary, it provides a useful basis for evaluating the overall T cell epitope destroying ability of PEP and BBM. Based on this analysis, PEP treatment alone completely detoxifies gluten from the viewpoint of a majority of the celiac lesion derived T cell lines (8 out of 14); the same PEP-treated gluten can be considered partially detoxified as assessed by the remaining T cell lines. No case was identified where the antigenicity of gluten was unaffected by PEP treatment. The synergistic effect of BBM is also apparent, since 12 out of 14 T cell lines indicated a complete destruction of T cell epitopes when treated with PEP and BBM in sequence; the remaining two T cell lines showed some residual activity to the PEP and BBM treated gluten. In contrast, BBM treatment alone led to complete abrogation of T cell response for only one line (TCL 451.1.1) and partial abrogation of T cell responses in only six lines. The responses of the remaining lines were unaltered by BBM treatment of gluten. Together these results make a compelling case for the potential benefit of PEP in the digestive system of a Celiac Sprue patient.

TABLE 5

| T cell line | PEP alone | BBM alone | PEP + BBM |
|---|---|---|---|
| 421.1.4 | 1% | 4% | 1% |
| 422.02.4.2 | 1% | 31% | 1% |
| 432.2.1 | 1% | 65% | 1% |
| 437.1.3 | 1% | 16% | 1% |
| 437.1.1 | 1% | 5% | 1% |

TABLE 5-continued

| T cell line | PEP alone | BBM alone | PEP + BBM |
|---|---|---|---|
| 446.1.3 | 1% | 5% | 1% |
| 451.1.1 | 1% | 1% | 1% |
| 461.02.1.4 | 5% | 11% | 1% |
| 482.1.4 | 4% | 28% | 1% |
| 488.3.1 | 2% | 58% | 2% |
| 491.1.3 | 2% | >100% | 2% |
| 494.1.1 | 7% | 12% | 1% |
| 496.1.2 | 5% | 42% | 2% |
| 502.1.2 | 11% | 68% | 10% |

T cell assays-T cell clones

Since individual T cell clones recognize distinct epitopes from gluten, they provide an excellent assay system to quantify the abundance of that epitope in a complex but physiologically relevant material such as proteolyzed gluten. Eight T cell clones were characterized using the same assay set-up as in the case of polyclonal T cell lines (FIG. 6A). The kinetics of the destruction of gluten epitopes were also monitored by exposing gluten to PEP for varying time periods while keeping the BBM exposure constant (FIG. 6B). A pattern emerges from this data set. The α-gliadin epitopes are highly susceptible to PEP-mediated destruction, the α-II and α-III more so than the α-1. PEP-treated gluten retains some activity for the α-I specific intestinal T cell clone 387E9 even after 60 min PEP treatment, whereas the peptides recognized by the α-II specific T cell clone 430.1.135 and the α-III specific 370E3.19 are almost completely destroyed at the earliest time point (FIGS. 6A and 6B). This is consistent with the notion that the immunodominant α-G 33 peptide is destroyed by PEP (12).

In contrast, destruction of some γ-gliadin epitopes is considerably less efficient by the *Flavobacterium meningosepticum* PEP. Indeed, BBM treatment alone has a dramatic effect on the γ-I and IV epitopes (TCC 423.1.3.8 and TCC 430.1.112), a partial effect on the γ-II and γ-III epitopes (TCC 430.1.41 and 430.1.134), but no effect on the γ-VI-epitope (FIG. 6B). Whereas the γ-II epitope is rapidly eliminated by this PEP after only 10 min, gluten fragments containing the γ-II and γ-VI epitopes persist for longer durations.

Here we have taken a significant step forward through the detailed chemical and biological analysis of the effects of PEP on whole gluten as found in a typical grocery store. Our chemical analyses involved high-resolution chromatographic and mass spectroscopic procedures, whereas our biological analyses involved the use of DQ2-restricted, gluten-responsive T cells that are the hallmarks of celiac lesions in the small intestine. In addition to lending further support to the proposal that immunogenic fragments of gluten are also proteolytically resistant, our results demonstrate that a suitable PEP, or a cocktail of PEPs with complementary substrate specificities, may be an effective way to render gluten harmless for many Celiac Sprue patients.

LC-MS/MS of whole gluten proteolyzed under various conditions demonstrated that a majority of epitope-containing peptides were between 21 and 30 residues in length (26 out of 44, 60%), although a few peptides (n=5) were longer than 30 residues. In contrast, the majority of non-antigenic peptides were between 11 and 20 residues in length. There may be a bias in the length assessment as reliable detection of long peptide sequences using ion trap MS/MS detection is limited due to incomplete fragmentation of longer peptides. The problem is exacerbated for peptides rich in Pro and Gln residues, as they inhibit complete fragmentation. Finally, there are significant limitations associated with the quantitative capabilities of our LC-MS/MS based assessment of toxicity. For example, the multiple hits for the γ-VI epitope are likely due to the large number of parent sequences harboring this epitope in the Entrez Protein database; they may not necessarily imply an exceptionally high abundance of this sequence. Quantitation of fragments by MS requires the use of internal standards (19, 20), which are difficult to generate for complex, uncharacterized and variable materials such as grocery store gluten. Notwithstanding these limitations, we have employed LC-MS/MS to demonstrate that PEP treatment and, to a lesser extent, BBM treatment, results in a substantial reduction of abundance of immunogenic peptides in gluten that has been pre-treated with pepsin and pancreatic enzymes.

T cells derived from small intestinal biopsy samples of Celiac Sprue patients are exquisitely sensitive and accurate monitors of the inflammatory potential of a processed gluten sample. In the absence of an animal model for Celiac Sprue, such T cell experiments are the best approximation for the toxic effects of gluten in Celiac patients. Both monoclonal and polyclonal T cell samples have been utilized in this study to evaluate the scope of PEP therapy for Celiac Sprue. Our results (FIGS. 4 and 5) have confirmed that gluten pre-digested by pepsin and the pancreatic enzymes (PTCEC) retains considerable toxicity that in most cases cannot be eliminated even after prolonged treatment with intestinal brush border membrane (BBM) peptidases. Presumably this is due to the combination of length and proline-rich character of a typical immunogenic gluten peptide.

In contrast, in many cases PEP alone can be enough to achieve complete detoxification without the need for exposure to BBM, whereas in some cases, although PEP treatment results in partial detoxification of gluten, the action of BBM peptidases is necessary to achieve complete detoxification. These findings reinforce the heterogeneity of disease-associated T cells among Celiac Sprue patients, which in turn may forebode the heterogeneity of patient response to a selected PEP such as the *Flavobacterium meningosepticum* enzyme. For example, to the extent that the observed T cell responses in FIGS. 4 and 5 accurately reflect in vivo conditions, one might predict (Table 5) that patients 421, 422, 432, 437, 446, 451 and 491 would respond well to PEP treatment. Additionally, patients 461, 482, 488, 494 and 496 may also derive some benefit from PEP treatment, although such benefit would require healthy small intestinal mucosa with active BBM peptidases. T cell lines such as these provide a convenient assay for the identification of secondary enzymes that act in concert with the *F. meningosepticum* PEP to further accelerate gluten detoxification. Finally, patient 502 is unlikely to stay in remission when challenged with gluten even when treated with an otherwise effective PEP. This cell line therefore serves as a suitable assay system to identify either a secondary enzyme capable of acting in concert with the *F. meningosepticum* PEP or an alternate enzyme catalyst for gluten detoxification.

In addition to polyclonal T cell lines, monoclonal T cells are also valuable reagents for evaluating the efficacy of PEP. As summarized in FIG. 6, they provide a complementary picture of gluten detoxification when compared with LC-MS/MS analysis and polyclonal T cell line assays. In particular, since their epitope specificity has been previously characterized, they serve as excellent reporters of the persistence of individual epitopes in a complex gluten mixture that has been treated with a given PEP. For example, from analysis of 8 different T cell clones, it can be concluded that, whereas the *F. meningosepticum* enzyme has high specificity for α-gliadin epitopes, it has lower specificity for γ-gliadin epitopes. For example, epitopes γ-II (TG2-treated IQPQQPAQL) and γ-VI (TG2-treated PQQPFPQQPQQ) recognized by the intestinal T cell clones 430.1.41 and 387.3, respectively, seem to be stable against treatment with both PEP and BBM. For the γ-VI epitope, our LC-MS/MS analysis supports this notion. It is unclear why these γ-gliadin derived peptides are more resistant to cleavage by *F. meningosepticum* PEP than other T cell epitopes. It could be noted however that these two epitopes, despite their resistance to the PEP and BBM treatment, are not frequently recognized by intestinal T cells. This could be related to low levels of these proteins in ingested gluten, inefficient presentation by DQ2+ antigen presenting cells in the celiac lesions and/or lack of T cells with appropriate T cell receptors. Encouragingly, parallel studies have revealed that PEPs from different sources have different substrate specificities, both with regard to cleavage sites and substrate chain lengths. Thus, there remains considerable potential for combining PEPs with complementary substrate specificities, or for screening and/or engineering PEPs with optimized ability to render gluten non-stimulatory to intestinal T cells in Celiac Sprue patients.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. A purified gluten oligopeptide consisting of an amino acid sequence selected from the group consisting of SEQ ID NO:32; SEQ ID NO:35; SEQ ID NO:39; SEQ ID NO:40; SEQ ID NO:42; SEQ ID NO:44; SEQ ID NO:46; SEQ ID NO:47; SEQ ID NO:48; SEQ ID NO:50; SEQ ID NO:51; SEQ ID NO:52; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:64; SEQ ID NO:65; SEQ ID NO:66; SEQ ID NO:67; SEQ ID NO:68; SEQ ID NO:69; SEQ ID NO:72; SEQ ID NO:73; SEQ ID NO:74; SEQ ID NO:75; SEQ ID NO:76; SEQ ID NO:78; SEQ ID NO:80; SEQ ID NO:82; SEQ ID NO:83; and SEQ ID NO:84.

2. The oligopeptide of claim 1, further comprising a label for chromogenic assays.

3. A purified gluten oligopeptide consisting of an amino acid sequence selected from the group consisting of SEQ ID NO:46; SEQ ID NO:47; SEQ ID NO:48; SEQ ID NO:50; SEQ ID NO:51; SEQ ID NO:52; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:64; SEQ ID NO:65; SEQ ID NO:66; SEQ ID NO:67; SEQ ID NO:68; SEQ ID NO:69; SEQ ID NO:72; and SEQ ID NO:73.

4. The oligopeptide of claim 3, further comprising a label for chromogenic assays.

5. A purified gluten oligopeptide having a sequence as selected from the group consisting of SEQ ID NO:32; SEQ ID NO:35; SEQ ID NO:39; SEQ ID NO:40; SEQ ID NO:42; SEQ ID NO:44; SEQ ID NO:46; SEQ ID NO:47; SEQ ID NO:48; SEQ ID NO:50; SEQ ID NO:51; SEQ ID NO:52; SEQ ID NO:54; SEQ ID NO:55; SEQ ID NO:56; SEQ ID NO:57; SEQ ID NO:58; SEQ ID NO:59; SEQ ID NO:60; SEQ ID NO:61; SEQ ID NO:64; SEQ ID NO:65; SEQ ID NO:66; SEQ ID NO:67; SEQ ID NO:68; SEQ ID NO:69; SEQ ID NO:72; SEQ ID NO:73; SEQ ID NO:74; SEQ ID NO:75; SEQ ID NO:76; SEQ ID NO:78; SEQ ID NO:80; SEQ ID NO:82; SEQ ID NO:83; and SEQ ID NO:84; which oligopeptide is covalently linked to a mammalian tTGase.

6. The oligopeptide of claim 5, wherein said mammalian tTGase is selected from the group consisting of a human, bovine, equine, and porcine tTGase.

7. The oligopeptide of claim 6, wherein said tTGase is covalently linked to said oligopeptide at a site of deamidation.

* * * * *

SEQUENCE LISTING

```
<160> NUMBER OF SEQ ID NOS: 86

<210> SEQ ID NO 1
<211> LENGTH: 13
<212> TYPE: PRT
<213> ORGANISM: Artificial Sequence
<220> FEATURE:
<223> OTHER INFORMATION: analog of wheat protein

<400> SEQUENCE: 1

Gln Leu Gln Pro Phe Pro Gln Pro Glu Leu Pro Tyr Pro
 1               5                  10

<210> SEQ ID NO 2
<211> LENGTH: 7
<212> TYPE: PRT
<213> ORGANISM: Artificial Sequence
<220> FEATURE:
<223> OTHER INFORMATION: analog of wheat protein

<400> SEQUENCE: 2

Pro Gln Pro Glu Leu Pro Tyr
 1               5

<210> SEQ ID NO 3
<211> LENGTH: 10
<212> TYPE: PRT
<213> ORGANISM: Artificial Sequence
<220> FEATURE:
<223> OTHER INFORMATION: analog of wheat protein

<400> SEQUENCE: 3

Pro Phe Pro Gln Pro Glu Leu Pro Tyr Pro
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: analog of wheat protein

<400> SEQUENCE: 4

Pro Gln Pro Glu Leu Pro Tyr Pro Gln Pro Gln Leu Pro
 1               5                  10
```

```
<210> SEQ ID NO 5
<211> LENGTH: 11
<212> TYPE: PRT
<213> ORGANISM: Artificial Sequence
<220> FEATURE:
<223> OTHER INFORMATION: analog of wheat protein

<400> SEQUENCE: 5

Pro Gln Gln Ser Phe Pro Glu Gln Gln Pro Pro
 1               5                  10

<210> SEQ ID NO 6
<211> LENGTH: 14
<212> TYPE: PRT
<213> ORGANISM: Artificial Sequence
<220> FEATURE:
<223> OTHER INFORMATION: analog of wheat protein

<400> SEQUENCE: 6

Val Gln Gly Gln Gly Ile Ile Gln Pro Glu Gln Pro Ala Gln
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: analog of wheat protein

<400> SEQUENCE: 7

Phe Pro Glu Gln Pro Gln Gln Pro Tyr Pro Gln Gln Pro
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: analog of wheat protein

<400> SEQUENCE: 8

Phe Pro Gln Gln Pro Glu Gln Pro Tyr Pro Gln Gln Pro
 1               5                  10

<210> SEQ ID NO 9
<211> LENGTH: 12
<212> TYPE: PRT
<213> ORGANISM: Artificial Sequence
<220> FEATURE:
<223> OTHER INFORMATION: analog of wheat protein

<400> SEQUENCE: 9

Phe Ser Gln Pro Glu Gln Glu Phe Pro Gln Pro Gln
 1               5                  10

<210> SEQ ID NO 10
<211> LENGTH: 7
<212> TYPE: PRT
<213> ORGANISM: Artificial Sequence
<220> FEATURE:
<223> OTHER INFORMATION: analog of wheat protein

<400> SEQUENCE: 10

Pro Gln Pro Gln Leu Pro Tyr
 1               5

<210> SEQ ID NO 11
```

```
<211> LENGTH: 9
<212> TYPE: PRT
<213> ORGANISM: Artificial Sequence
<220> FEATURE:
<223> OTHER INFORMATION: analog of wheat protein

<400> SEQUENCE: 11

Pro Phe Pro Gln Pro Gln Leu Pro Tyr
1               5

<210> SEQ ID NO 12
<211> LENGTH: 33
<212> TYPE: PRT
<213> ORGANISM: Artificial Sequence
<220> FEATURE:
<223> OTHER INFORMATION: analog of wheat protein

<400> SEQUENCE: 12

Leu Gln Leu Gln Pro Phe Pro Gln Pro Gln Leu Pro Tyr Pro Gln Pro
1               5                   10                  15

Gln Leu Pro Tyr Pro Gln Pro Gln Leu Pro Tyr Pro Gln Pro Gln Pro
            20                  25                  30

Phe

<210> SEQ ID NO 13
<211> LENGTH: 9
<212> TYPE: PRT
<213> ORGANISM: Artificial Sequence
<220> FEATURE:
<223> OTHER INFORMATION: analog of wheat protein

<400> SEQUENCE: 13

Pro Tyr Pro Gln Pro Gln Leu Pro Tyr
1               5

<210> SEQ ID NO 14
<211> LENGTH: 9
<212> TYPE: PRT
<213> ORGANISM: Artificial Sequence
<220> FEATURE:
<223> OTHER INFORMATION: analog of wheat protein

<400> SEQUENCE: 14

Pro Gln Pro Gln Leu Pro Tyr Pro Gln
1               5

<210> SEQ ID NO 15
<211> LENGTH: 9
<212> TYPE: PRT
<213> ORGANISM: Artificial Sequence
<220> FEATURE:
<223> OTHER INFORMATION: analog of wheat protein

<400> SEQUENCE: 15

Phe Arg Pro Gln Gln Pro Tyr Pro Gln
1               5

<210> SEQ ID NO 16
<211> LENGTH: 9
<212> TYPE: PRT
<213> ORGANISM: Artificial Sequence
<220> FEATURE:
<223> OTHER INFORMATION: analog of wheat protein

<400> SEQUENCE: 16

Pro Gln Gln Ser Phe Pro Gln Gln Gln
```

```
<210> SEQ ID NO 17
<211> LENGTH: 9
<212> TYPE: PRT
<213> ORGANISM: Artificial Sequence
<220> FEATURE:
<223> OTHER INFORMATION: analog of wheat protein

<400> SEQUENCE: 17

Ile Gln Pro Gln Gln Pro Ala Gln Leu
 1               5

<210> SEQ ID NO 18
<211> LENGTH: 9
<212> TYPE: PRT
<213> ORGANISM: Artificial Sequence
<220> FEATURE:
<223> OTHER INFORMATION: analog of wheat protein

<400> SEQUENCE: 18

Gln Gln Pro Gln Gln Pro Tyr Pro Gln
 1               5

<210> SEQ ID NO 19
<211> LENGTH: 9
<212> TYPE: PRT
<213> ORGANISM: Artificial Sequence
<220> FEATURE:
<223> OTHER INFORMATION: analog of wheat protein

<400> SEQUENCE: 19

Ser Gln Pro Gln Gln Gln Phe Pro Gln
 1               5

<210> SEQ ID NO 20
<211> LENGTH: 9
<212> TYPE: PRT
<213> ORGANISM: Artificial Sequence
<220> FEATURE:
<223> OTHER INFORMATION: analog of wheat protein

<400> SEQUENCE: 20

Gln Gln Pro Phe Pro Gln Gln Pro Gln
 1               5

<210> SEQ ID NO 21
<211> LENGTH: 9
<212> TYPE: PRT
<213> ORGANISM: Artificial Sequence
<220> FEATURE:
<223> OTHER INFORMATION: analog of wheat protein

<400> SEQUENCE: 21

Pro Tyr Pro Gln Gln Pro Gln Gln Pro
 1               5

<210> SEQ ID NO 22
<211> LENGTH: 9
<212> TYPE: PRT
<213> ORGANISM: Artificial Sequence
<220> FEATURE:
<223> OTHER INFORMATION: analog of wheat protein

<400> SEQUENCE: 22

Gln Ile Pro Gln Gln Pro Gln Gln Phe
 1               5
```

<210> SEQ ID NO 23
<211> LENGTH: 9
<212> TYPE: PRT
<213> ORGANISM: Artificial Sequence
<220> FEATURE:
<223> OTHER INFORMATION: analog of wheat protein

<400> SEQUENCE: 23

Gln Leu Pro Gln Gln Pro Gln Gln Phe
1               5

<210> SEQ ID NO 24
<211> LENGTH: 9
<212> TYPE: PRT
<213> ORGANISM: Artificial Sequence
<220> FEATURE:
<223> OTHER INFORMATION: analog of wheat protein

<400> SEQUENCE: 24

Pro Phe Ser Gln Gln Gln Gln Pro Val
1               5

<210> SEQ ID NO 25
<211> LENGTH: 9
<212> TYPE: PRT
<213> ORGANISM: Artificial Sequence
<220> FEATURE:
<223> OTHER INFORMATION: analog of wheat protein

<400> SEQUENCE: 25

Pro Phe Ser Gln Gln Gln Gln Pro Ile
1               5

<210> SEQ ID NO 26
<211> LENGTH: 12
<212> TYPE: PRT
<213> ORGANISM: Artificial Sequence
<220> FEATURE:
<223> OTHER INFORMATION: analog of wheat protein

<400> SEQUENCE: 26

Gln Leu Gln Pro Phe Pro Gln Pro Gln Leu Pro Tyr
1               5                   10

<210> SEQ ID NO 27
<211> LENGTH: 14
<212> TYPE: PRT
<213> ORGANISM: Artificial Sequence
<220> FEATURE:
<223> OTHER INFORMATION: analog of wheat protein

<400> SEQUENCE: 27

Pro Gln Pro Gln Leu Pro Tyr Pro Gln Pro Gln Leu Pro Tyr
1               5                   10

<210> SEQ ID NO 28
<211> LENGTH: 15
<212> TYPE: PRT
<213> ORGANISM: Artificial Sequence
<220> FEATURE:
<223> OTHER INFORMATION: analog of wheat protein

<400> SEQUENCE: 28

Gln Pro Gln Gln Pro Gln Gln Ser Phe Pro Gln Gln Gln Arg Pro
1               5                   10                  15

```
<210> SEQ ID NO 29
<211> LENGTH: 11
<212> TYPE: PRT
<213> ORGANISM: Artificial Sequence
<220> FEATURE:
<223> OTHER INFORMATION: analog of wheat protein

<400> SEQUENCE: 29

Gly Ile Ile Gln Pro Gln Gln Pro Ala Gln Leu
 1               5                  10

<210> SEQ ID NO 30
<211> LENGTH: 20
<212> TYPE: PRT
<213> ORGANISM: Artificial Sequence
<220> FEATURE:
<223> OTHER INFORMATION: analog of wheat protein

<400> SEQUENCE: 30

Leu Gln Pro Gln Gln Pro Phe Pro Gln Gln Pro Gln Gln Pro Tyr Pro
 1               5                  10                  15

Gln Gln Pro Gln
            20

<210> SEQ ID NO 31
<211> LENGTH: 21
<212> TYPE: PRT
<213> ORGANISM: Artificial Sequence
<220> FEATURE:
<223> OTHER INFORMATION: analog of wheat protein
<220> FEATURE:
<221> NAME/KEY: VARIANT
<222> LOCATION: (3)...(3)
<223> OTHER INFORMATION: Xaa = I or L
<220> FEATURE:
<221> NAME/KEY: VARIANT
<222> LOCATION: (8)...(8)
<223> OTHER INFORMATION: Xaa = I or L
<220> FEATURE:
<221> NAME/KEY: VARIANT
<222> LOCATION: (14)...(14)
<223> OTHER INFORMATION: Xaa = I or L

<400> SEQUENCE: 31

Gln Gln Xaa Ser Gln Pro Gln Xaa Pro Gln Gln Gln Gln Xaa Pro Gln
 1               5                  10                  15

Gln Pro Gln Gln Phe
            20

<210> SEQ ID NO 32
<211> LENGTH: 29
<212> TYPE: PRT
<213> ORGANISM: Artificial Sequence
<220> FEATURE:
<223> OTHER INFORMATION: analog of wheat protein

<400> SEQUENCE: 32

Gln Pro Phe Pro Gln Pro Gln Leu Pro Tyr Pro Gln Pro Gln Leu Pro
 1               5                  10                  15

Tyr Pro Gln Pro Gln Leu Pro Tyr Pro Gln Pro Gln Pro
            20                  25

<210> SEQ ID NO 33
<211> LENGTH: 29
<212> TYPE: PRT
<213> ORGANISM: Artificial Sequence
<220> FEATURE:
```

-continued

```
<223> OTHER INFORMATION: analog of wheat protein

<400> SEQUENCE: 33

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro
            20                  25

<210> SEQ ID NO 34
<211> LENGTH: 29
<212> TYPE: PRT
<213> ORGANISM: Artificial Sequence
<220> FEATURE:
<223> OTHER INFORMATION: analog of wheat protein

<400> SEQUENCE: 34

Gln Pro Phe Pro Gln Pro Gln Leu Pro Tyr Pro Gln Pro Gln Leu Pro
1               5                   10                  15

Tyr Pro Gln Pro Gln Leu Pro Tyr Pro Gln Pro Gln Pro
            20                  25

<210> SEQ ID NO 35
<211> LENGTH: 28
<212> TYPE: PRT
<213> ORGANISM: Artificial Sequence
<220> FEATURE:
<223> OTHER INFORMATION: analog of wheat protein

<400> SEQUENCE: 35

Pro Phe Pro Gln Pro Gln Leu Pro Tyr Pro Gln Pro Gln Leu Pro Tyr
1               5                   10                  15

Pro Gln Pro Gln Leu Pro Tyr Pro Gln Pro Gln Pro
            20                  25

<210> SEQ ID NO 36
<211> LENGTH: 28
<212> TYPE: PRT
<213> ORGANISM: Artificial Sequence
<220> FEATURE:
<223> OTHER INFORMATION: analog of wheat protein

<400> SEQUENCE: 36

Pro Phe Pro Gln Pro Gln Leu Pro Tyr Pro Gln Pro Gln Leu Pro Tyr
1               5                   10                  15

Pro Gln Pro Gln Leu Pro Tyr Pro Gln Pro Gln Pro
            20                  25

<210> SEQ ID NO 37
<211> LENGTH: 28
<212> TYPE: PRT
<213> ORGANISM: Artificial Sequence
<220> FEATURE:
<223> OTHER INFORMATION: analog of wheat protein

<400> SEQUENCE: 37

Pro Phe Pro Gln Pro Gln Leu Pro Tyr Pro Gln Pro Gln Leu Pro Tyr
1               5                   10                  15

Pro Gln Pro Gln Leu Pro Tyr Pro Gln Pro Gln Pro
            20                  25

<210> SEQ ID NO 38
<211> LENGTH: 33
<212> TYPE: PRT
<213> ORGANISM: Artificial Sequence
```

```
<220> FEATURE:
<223> OTHER INFORMATION: analog of wheat protein

<400> SEQUENCE: 38

Leu Gln Leu Gln Pro Phe Pro Gln Pro Gln Leu Pro Tyr Pro Gln Pro
 1               5                  10                  15

Gln Leu Pro Tyr Pro Gln Pro Gln Leu Pro Tyr Pro Gln Pro Gln Pro
            20                  25                  30

Phe

<210> SEQ ID NO 39
<211> LENGTH: 19
<212> TYPE: PRT
<213> ORGANISM: Artificial Sequence
<220> FEATURE:
<223> OTHER INFORMATION: analog of wheat protein

<400> SEQUENCE: 39

Gln Pro Phe Pro Gln Pro Gln Leu Pro Tyr Pro Gln Pro Gln Pro Phe
 1               5                  10                  15

Arg Pro Gln

<210> SEQ ID NO 40
<211> LENGTH: 26
<212> TYPE: PRT
<213> ORGANISM: Artificial Sequence
<220> FEATURE:
<223> OTHER INFORMATION: analog of wheat protein

<400> SEQUENCE: 40

Pro Phe Pro Gln Pro Gln Leu Pro Tyr Leu Gln Pro Gln Pro Phe Arg
 1               5                  10                  15

Pro Gln Gln Pro Tyr Pro Gln Pro Gln Pro
            20                  25

<210> SEQ ID NO 41
<211> LENGTH: 26
<212> TYPE: PRT
<213> ORGANISM: Artificial Sequence
<220> FEATURE:
<223> OTHER INFORMATION: analog of wheat protein

<400> SEQUENCE: 41

Pro Phe Pro Gln Pro Gln Leu Pro Tyr Leu Gln Pro Gln Pro Phe Arg
 1               5                  10                  15

Pro Gln Gln Pro Tyr Pro Gln Pro Gln Pro
            20                  25

<210> SEQ ID NO 42
<211> LENGTH: 20
<212> TYPE: PRT
<213> ORGANISM: Artificial Sequence
<220> FEATURE:
<223> OTHER INFORMATION: analog of wheat protein

<400> SEQUENCE: 42

Gln Pro Phe Pro Gln Pro Gln Leu Pro Tyr Pro Gln Pro Gln Pro Phe
 1               5                  10                  15

Arg Pro Gln Gln
            20

<210> SEQ ID NO 43
<211> LENGTH: 20
```

```
<212> TYPE: PRT
<213> ORGANISM: Artificial Sequence
<220> FEATURE:
<223> OTHER INFORMATION: analog of wheat protein

<400> SEQUENCE: 43

Gln Pro Phe Pro Gln Pro Gln Leu Pro Tyr Pro Gln Pro Gln Pro Phe
 1               5                  10                  15

Arg Pro Gln Gln
         20

<210> SEQ ID NO 44
<211> LENGTH: 29
<212> TYPE: PRT
<213> ORGANISM: Artificial Sequence
<220> FEATURE:
<223> OTHER INFORMATION: analog of wheat protein

<400> SEQUENCE: 44

Pro Leu Phe Gln Leu Val Gln Gly Gln Gly Ile Ile Gln Pro Gln Gln
 1               5                  10                  15

Pro Ala Gln Leu Glu Val Ile Arg Ser Leu Val Leu Gly
         20                  25

<210> SEQ ID NO 45
<211> LENGTH: 29
<212> TYPE: PRT
<213> ORGANISM: Artificial Sequence
<220> FEATURE:
<223> OTHER INFORMATION: analog of wheat protein

<400> SEQUENCE: 45

Pro Leu Phe Gln Leu Val Gln Gly Gln Gly Ile Ile Gln Pro Gln Gln
 1               5                  10                  15

Pro Ala Gln Leu Glu Val Ile Arg Ser Leu Val Leu Gly
         20                  25

<210> SEQ ID NO 46
<211> LENGTH: 41
<212> TYPE: PRT
<213> ORGANISM: Artificial Sequence
<220> FEATURE:
<223> OTHER INFORMATION: analog of wheat protein

<400> SEQUENCE: 46

Gln Val Pro Gln Pro Gln Gln Pro Gln Gln Pro Phe Leu Gln Pro Gln
 1               5                  10                  15

Gln Pro Phe Pro Gln Gln Pro Gln Gln Pro Phe Pro Gln Thr Gln Gln
         20                  25                  30

Pro Gln Gln Pro Phe Pro Gln Gln Pro
         35                  40

<210> SEQ ID NO 47
<211> LENGTH: 30
<212> TYPE: PRT
<213> ORGANISM: Artificial Sequence
<220> FEATURE:
<223> OTHER INFORMATION: analog of wheat protein

<400> SEQUENCE: 47

Phe Leu Gln Pro Gln Gln Pro Phe Pro Gln Gln Pro Gln Gln Pro Phe
 1               5                  10                  15

Pro Gln Thr Gln Gln Pro Gln Gln Pro Phe Pro Gln Gln Pro
         20                  25                  30
```

<210> SEQ ID NO 48
<211> LENGTH: 24
<212> TYPE: PRT
<213> ORGANISM: Artificial Sequence
<220> FEATURE:
<223> OTHER INFORMATION: analog of wheat protein

<400> SEQUENCE: 48

Pro Gln Pro Gln Gln Pro Gln Gln Pro Phe Leu Gln Pro Gln Gln Pro
1               5                   10                  15

Phe Pro Gln Gln Pro Gln Gln Pro
            20

<210> SEQ ID NO 49
<211> LENGTH: 24
<212> TYPE: PRT
<213> ORGANISM: Artificial Sequence
<220> FEATURE:
<223> OTHER INFORMATION: analog of wheat protein

<400> SEQUENCE: 49

Pro Gln Pro Gln Gln Pro Gln Gln Pro Phe Leu Gln Pro Gln Gln Pro
1               5                   10                  15

Phe Pro Gln Gln Pro Gln Gln Pro
            20

<210> SEQ ID NO 50
<211> LENGTH: 22
<212> TYPE: PRT
<213> ORGANISM: Artificial Sequence
<220> FEATURE:
<223> OTHER INFORMATION: analog of wheat protein

<400> SEQUENCE: 50

Pro Gln Gln Pro Gln Gln Pro Phe Leu Gln Pro Gln Gln Pro Phe Pro
1               5                   10                  15

Gln Gln Pro Gln Gln Pro
            20

<210> SEQ ID NO 51
<211> LENGTH: 18
<212> TYPE: PRT
<213> ORGANISM: Artificial Sequence
<220> FEATURE:
<223> OTHER INFORMATION: analog of wheat protein

<400> SEQUENCE: 51

Pro Phe Leu Gln Pro Gln Gln Pro Phe Pro Gln Gln Pro Gln Gln Pro
1               5                   10                  15

Phe Pro

<210> SEQ ID NO 52
<211> LENGTH: 17
<212> TYPE: PRT
<213> ORGANISM: Artificial Sequence
<220> FEATURE:
<223> OTHER INFORMATION: analog of wheat protein

<400> SEQUENCE: 52

Leu Gln Pro Gln Gln Pro Phe Pro Gln Gln Pro Gln Gln Pro Phe Pro
1               5                   10                  15

Gln

```
<210> SEQ ID NO 53
<211> LENGTH: 17
<212> TYPE: PRT
<213> ORGANISM: Artificial Sequence
<220> FEATURE:
<223> OTHER INFORMATION: analog of wheat protein

<400> SEQUENCE: 53

Leu Gln Pro Gln Gln Pro Phe Pro Gln Gln Pro Gln Gln Pro Phe Pro
 1               5                  10                  15

Gln

<210> SEQ ID NO 54
<211> LENGTH: 32
<212> TYPE: PRT
<213> ORGANISM: Artificial Sequence
<220> FEATURE:
<223> OTHER INFORMATION: analog of wheat protein

<400> SEQUENCE: 54

Gln Gln Ser Glu Gln Ile Ile Pro Gln Gln Leu Gln Gln Pro Phe Pro
 1               5                  10                  15

Leu Gln Pro Gln Gln Pro Phe Pro Gln Gln Pro Gln Gln Pro Phe Pro
            20                  25                  30

<210> SEQ ID NO 55
<211> LENGTH: 29
<212> TYPE: PRT
<213> ORGANISM: Artificial Sequence
<220> FEATURE:
<223> OTHER INFORMATION: analog of wheat protein

<400> SEQUENCE: 55

Gln Pro Phe Pro Leu Gln Pro Gln Gln Pro Phe Pro Gln Gln Pro Gln
 1               5                  10                  15

Gln Pro Phe Pro Gln Pro Gln Gln Pro Ile Pro Val Gln
            20                  25

<210> SEQ ID NO 56
<211> LENGTH: 27
<212> TYPE: PRT
<213> ORGANISM: Artificial Sequence
<220> FEATURE:
<223> OTHER INFORMATION: analog of wheat protein

<400> SEQUENCE: 56

Gln Pro Phe Pro Leu Gln Pro Gln Gln Pro Phe Pro Gln Gln Pro Gln
 1               5                  10                  15

Gln Pro Phe Pro Gln Pro Gln Gln Pro Ile Pro
            20                  25

<210> SEQ ID NO 57
<211> LENGTH: 40
<212> TYPE: PRT
<213> ORGANISM: Artificial Sequence
<220> FEATURE:
<223> OTHER INFORMATION: analog of wheat protein

<400> SEQUENCE: 57

Pro Gln Gln Pro Gln Gln Pro Phe Pro Gln Thr Gln Gln Pro Gln Gln
 1               5                  10                  15

Pro Phe Pro Gln Gln Pro Gln Gln Pro Phe Pro Gln Thr Gln Gln Pro
            20                  25                  30
```

Gln Gln Pro Phe Pro Gln Gln Pro
        35                  40

<210> SEQ ID NO 58
<211> LENGTH: 36
<212> TYPE: PRT
<213> ORGANISM: Artificial Sequence
<220> FEATURE:
<223> OTHER INFORMATION: analog of wheat protein

<400> SEQUENCE: 58

Thr Gln Gln Pro Gln Gln Pro Phe Pro Gln Gln Pro Gln Gln Pro Phe
1               5                   10                  15

Pro Gln Thr Gln Gln Pro Gln Gln Pro Phe Pro Gln Gln Pro Gln Gln
            20                  25                  30

Pro Phe Pro Gln
        35

<210> SEQ ID NO 59
<211> LENGTH: 20
<212> TYPE: PRT
<213> ORGANISM: Artificial Sequence
<220> FEATURE:
<223> OTHER INFORMATION: analog of wheat protein

<400> SEQUENCE: 59

Thr Gln Gln Pro Gln Gln Pro Phe Pro Gln Gln Pro Gln Gln Pro Phe
1               5                   10                  15

Pro Gln Thr Gln
            20

<210> SEQ ID NO 60
<211> LENGTH: 20
<212> TYPE: PRT
<213> ORGANISM: Artificial Sequence
<220> FEATURE:
<223> OTHER INFORMATION: analog of wheat protein

<400> SEQUENCE: 60

Phe Pro Gln Thr Gln Gln Pro Gln Gln Pro Phe Pro Gln Gln Pro Gln
1               5                   10                  15

Gln Pro Phe Pro
            20

<210> SEQ ID NO 61
<211> LENGTH: 18
<212> TYPE: PRT
<213> ORGANISM: Artificial Sequence
<220> FEATURE:
<223> OTHER INFORMATION: analog of wheat protein

<400> SEQUENCE: 61

Thr Gln Gln Pro Gln Gln Pro Phe Pro Gln Gln Pro Gln Gln Pro Phe
1               5                   10                  15

Pro Gln

<210> SEQ ID NO 62
<211> LENGTH: 18
<212> TYPE: PRT
<213> ORGANISM: Artificial Sequence
<220> FEATURE:
<223> OTHER INFORMATION: analog of wheat protein

<400> SEQUENCE: 62

```
Thr Gln Gln Pro Gln Gln Pro Phe Pro Gln Gln Pro Gln Gln Pro Phe
 1               5                  10                  15

Pro Gln
```

<210> SEQ ID NO 63
<211> LENGTH: 18
<212> TYPE: PRT
<213> ORGANISM: Artificial Sequence
<220> FEATURE:
<223> OTHER INFORMATION: analog of wheat protein

<400> SEQUENCE: 63

```
Thr Gln Gln Pro Gln Gln Pro Phe Pro Gln Gln Pro Gln Gln Pro Phe
 1               5                  10                  15

Pro Gln
```

<210> SEQ ID NO 64
<211> LENGTH: 17
<212> TYPE: PRT
<213> ORGANISM: Artificial Sequence
<220> FEATURE:
<223> OTHER INFORMATION: analog of wheat protein

<400> SEQUENCE: 64

```
Thr Gln Gln Pro Gln Gln Pro Phe Pro Gln Gln Pro Gln Gln Pro Phe
 1               5                  10                  15

Pro
```

<210> SEQ ID NO 65
<211> LENGTH: 40
<212> TYPE: PRT
<213> ORGANISM: Artificial Sequence
<220> FEATURE:
<223> OTHER INFORMATION: analog of wheat protein

<400> SEQUENCE: 65

```
Pro Gln Gln Leu Phe Pro Glu Leu Gln Gln Pro Ile Pro Gln Gln Pro
 1               5                  10                  15

Gln Gln Pro Phe Pro Leu Gln Pro Gln Gln Pro Phe Pro Gln Gln Pro
                20                  25                  30

Gln Gln Pro Phe Pro Gln Gln Pro
                35                  40
```

<210> SEQ ID NO 66
<211> LENGTH: 31
<212> TYPE: PRT
<213> ORGANISM: Artificial Sequence
<220> FEATURE:
<223> OTHER INFORMATION: analog of wheat protein

<400> SEQUENCE: 66

```
Phe Pro Glu Leu Gln Gln Pro Ile Pro Gln Gln Pro Gln Gln Pro Phe
 1               5                  10                  15

Pro Leu Gln Pro Gln Gln Pro Phe Pro Gln Gln Pro Gln Gln Pro
                20                  25                  30
```

<210> SEQ ID NO 67
<211> LENGTH: 29
<212> TYPE: PRT
<213> ORGANISM: Artificial Sequence
<220> FEATURE:
<223> OTHER INFORMATION: analog of wheat protein

<400> SEQUENCE: 67

-continued

Pro Gln Gln Pro Phe Pro Gln Gln Pro Gln Gln Pro Val Pro Gln Gln
 1               5                  10                  15

Ser Gln Gln Pro Phe Pro Gln Thr Gln Gln Pro Gln Gln
            20                  25

<210> SEQ ID NO 68
<211> LENGTH: 26
<212> TYPE: PRT
<213> ORGANISM: Artificial Sequence
<220> FEATURE:
<223> OTHER INFORMATION: analog of wheat protein

<400> SEQUENCE: 68

Gln Pro Gln Gln Pro Thr Pro Ile Gln Pro Gln Gln Pro Phe Pro Gln
 1               5                  10                  15

Gln Pro Gln Gln Pro Gln Gln Pro Phe Pro
            20                  25

<210> SEQ ID NO 69
<211> LENGTH: 18
<212> TYPE: PRT
<213> ORGANISM: Artificial Sequence
<220> FEATURE:
<223> OTHER INFORMATION: analog of wheat protein

<400> SEQUENCE: 69

Gln Pro Phe Pro Gln Gln Ser Gln Gln Pro Phe Pro Gln Gln Pro Gln
 1               5                  10                  15

Gln Ser

<210> SEQ ID NO 70
<211> LENGTH: 18
<212> TYPE: PRT
<213> ORGANISM: Artificial Sequence
<220> FEATURE:
<223> OTHER INFORMATION: analog of wheat protein

<400> SEQUENCE: 70

Gln Pro Phe Pro Gln Gln Ser Gln Gln Pro Phe Pro Gln Gln Pro Gln
 1               5                  10                  15

Gln Ser

<210> SEQ ID NO 71
<211> LENGTH: 18
<212> TYPE: PRT
<213> ORGANISM: Artificial Sequence
<220> FEATURE:
<223> OTHER INFORMATION: analog of wheat protein

<400> SEQUENCE: 71

Gln Pro Phe Pro Gln Gln Ser Gln Gln Pro Phe Pro Gln Gln Pro Gln
 1               5                  10                  15

Gln Ser

<210> SEQ ID NO 72
<211> LENGTH: 14
<212> TYPE: PRT
<213> ORGANISM: Artificial Sequence
<220> FEATURE:
<223> OTHER INFORMATION: analog of wheat protein

<400> SEQUENCE: 72

Gln Gln Ser Gln Gln Pro Phe Pro Gln Gln Pro Gln Gln Ser

<210> SEQ ID NO 73
<211> LENGTH: 15
<212> TYPE: PRT
<213> ORGANISM: Artificial Sequence
<220> FEATURE:
<223> OTHER INFORMATION: analog of wheat protein

<400> SEQUENCE: 73

Pro Gln Gln Pro Gln Gln Pro Phe Pro Gln Gln Pro Gln Gln Pro
 1               5                  10                  15

<210> SEQ ID NO 74
<211> LENGTH: 11
<212> TYPE: PRT
<213> ORGANISM: Artificial Sequence
<220> FEATURE:
<223> OTHER INFORMATION: analog of wheat protein

<400> SEQUENCE: 74

Gln Pro Gln Gln Pro Phe Pro Gln Gln Pro Gln
 1               5                  10

<210> SEQ ID NO 75
<211> LENGTH: 12
<212> TYPE: PRT
<213> ORGANISM: Artificial Sequence
<220> FEATURE:
<223> OTHER INFORMATION: analog of wheat protein

<400> SEQUENCE: 75

Pro Arg Gln Pro Tyr Pro Gln Gln Pro Gln Gln Pro
 1               5                  10

<210> SEQ ID NO 76
<211> LENGTH: 22
<212> TYPE: PRT
<213> ORGANISM: Artificial Sequence
<220> FEATURE:
<223> OTHER INFORMATION: analog of wheat protein

<400> SEQUENCE: 76

Ser Gln Gln Gln Gln Pro Pro Phe Ser Gln Gln Gln Pro Pro Phe Ser
 1               5                  10                  15

Gln Gln Gln Gln Pro Val
            20

<210> SEQ ID NO 77
<211> LENGTH: 22
<212> TYPE: PRT
<213> ORGANISM: Artificial Sequence
<220> FEATURE:
<223> OTHER INFORMATION: analog of wheat protein

<400> SEQUENCE: 77

Ser Gln Gln Gln Gln Pro Pro Phe Ser Gln Gln Gln Pro Pro Phe Ser
 1               5                  10                  15

Gln Gln Gln Gln Pro Val
            20

<210> SEQ ID NO 78
<211> LENGTH: 14
<212> TYPE: PRT
<213> ORGANISM: Artificial Sequence
<220> FEATURE:

<223> OTHER INFORMATION: analog of wheat protein

<400> SEQUENCE: 78

Ser Gln Gln Gln Pro Pro Phe Ser Gln Gln Gln Pro Val
1               5                   10

<210> SEQ ID NO 79
<211> LENGTH: 14
<212> TYPE: PRT
<213> ORGANISM: Artificial Sequence
<220> FEATURE:
<223> OTHER INFORMATION: analog of wheat protein

<400> SEQUENCE: 79

Ser Gln Gln Gln Pro Pro Phe Ser Gln Gln Gln Pro Val
1               5                   10

<210> SEQ ID NO 80
<211> LENGTH: 22
<212> TYPE: PRT
<213> ORGANISM: Artificial Sequence
<220> FEATURE:
<223> OTHER INFORMATION: analog of wheat protein

<400> SEQUENCE: 80

Ser Gln Gln Gln Leu Pro Pro Phe Ser Gln Gln Gln Pro Pro Phe Ser
1               5                   10                  15

Gln Gln Gln Gln Pro Val
            20

<210> SEQ ID NO 81
<211> LENGTH: 22
<212> TYPE: PRT
<213> ORGANISM: Artificial Sequence
<220> FEATURE:
<223> OTHER INFORMATION: analog of wheat protein

<400> SEQUENCE: 81

Ser Gln Gln Gln Leu Pro Pro Phe Ser Gln Gln Gln Pro Pro Phe Ser
1               5                   10                  15

Gln Gln Gln Gln Pro Val
            20

<210> SEQ ID NO 82
<211> LENGTH: 37
<212> TYPE: PRT
<213> ORGANISM: Artificial Sequence
<220> FEATURE:
<223> OTHER INFORMATION: analog of wheat protein

<400> SEQUENCE: 82

Pro Pro Phe Ser Gln Gln Gln Pro Val Leu Pro Gln Pro Pro
1               5                   10                  15

Phe Ser Gln Gln Gln Gln Gln Gln Gln Pro Pro Phe Ser Gln
            20                  25                  30

Gln Gln Gln Pro Val
        35

<210> SEQ ID NO 83
<211> LENGTH: 25
<212> TYPE: PRT
<213> ORGANISM: Artificial Sequence
<220> FEATURE:
<223> OTHER INFORMATION: analog of wheat protein -continued

```
<400> SEQUENCE: 83

Val Leu Pro Gln Gln Pro Pro Phe Ser Gln Gln Gln Pro Val Leu
 1               5                  10                 15

Pro Pro Gln Gln Ser Pro Phe Pro Gln
            20                  25

<210> SEQ ID NO 84
<211> LENGTH: 37
<212> TYPE: PRT
<213> ORGANISM: Artificial Sequence
<220> FEATURE:
<223> OTHER INFORMATION: analog of wheat protein

<400> SEQUENCE: 84

Phe Ser Gln Gln Gln Leu Pro Pro Phe Ser Gln Gln Leu Pro Pro Phe
 1               5                  10                 15

Ser Gln Gln Gln Gln Gln Val Leu Pro Gln Gln Pro Pro Phe Ser Gln
            20                  25                  30

Gln Gln Gln Pro Val
        35

<210> SEQ ID NO 85
<211> LENGTH: 37
<212> TYPE: PRT
<213> ORGANISM: Artificial Sequence
<220> FEATURE:
<223> OTHER INFORMATION: analog of wheat protein

<400> SEQUENCE: 85

Phe Ser Gln Gln Gln Leu Pro Pro Phe Ser Gln Gln Leu Pro Pro Phe
 1               5                  10                 15

Ser Gln Gln Gln Gln Gln Val Leu Pro Gln Gln Pro Pro Phe Ser Gln
            20                  25                  30

Gln Gln Gln Pro Val
        35

<210> SEQ ID NO 86
<211> LENGTH: 11
<212> TYPE: PRT
<213> ORGANISM: Artificial Sequence
<220> FEATURE:
<223> OTHER INFORMATION: analog of wheat protein

<400> SEQUENCE: 86

Pro Gln Gln Pro Phe Pro Gln Gln Pro Gln Gln
 1               5                  10
```